(12) United States Patent
Brown et al.

(10) Patent No.: US 6,369,064 B1
(45) Date of Patent: Apr. 9, 2002

(54) TRIAZOLO(4,5-D)PYRIMIDINE COMPOUNDS

(75) Inventors: Roger Brown, Leicestershire; Garry Pairaudeau, Lincolnshire; Brian Springthorpe; Stephen Thom, both of Loughborough; Paul Willis, Nottingham, all of (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/269,330

(22) PCT Filed: Feb. 5, 1999

(86) PCT No.: PCT/SE99/00154
§ 371 Date: Mar. 25, 1999
§ 102(e) Date: Mar. 25, 1999

(87) PCT Pub. No.: WO99/41254
PCT Pub. Date: Aug. 19, 1999

(30) Foreign Application Priority Data

Feb. 17, 1998 (SE) ................................................ 9800458
Oct. 26, 1998 (SE) ................................................ 9803669

(51) Int. Cl.$^7$ ..................... C07D 239/70; C07D 401/14; A61K 31/519
(52) U.S. Cl. ..................... 514/258; 544/254; 540/600
(58) Field of Search ..................... 544/254; 514/258; 540/600

(56) References Cited

FOREIGN PATENT DOCUMENTS

| EP | 0 215 759 A1 | 3/1987 |
|---|---|---|
| EP | 0 368 640 A2 | 5/1990 |
| EP | 0 368 640 A3 | 5/1990 |
| WO | 97/03084 | 1/1997 |
| WO | 98/28300 | 7/1998 |

*Primary Examiner*—John M. Ford
(74) *Attorney, Agent, or Firm*—Nixon & Vanderhye

(57) ABSTRACT

Triazolo[4,5-d]pyrimidine compounds are provided of the formula (I)

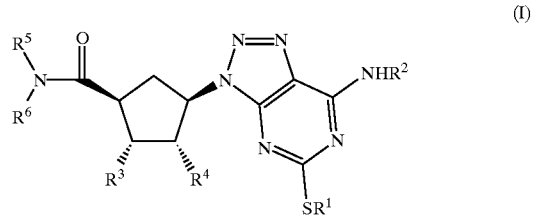

(I)

wherein $R^1$, $R^2$, $R^3$, $R^4$, $R^5$ and $R^6$ are as defined in the specification. Compositions containing the compounds are also provided, together with processes for their preparation and methods of use in the treatment of diseases, including myocardial infarction and unstable angina.

9 Claims, No Drawings

TRIAZOLO(4,5-D)PYRIMIDINE COMPOUNDS

This application is a 371 of PCT/SE99/00154, filed Feb. 5, 1999.

The present invention provides new triazolo[4,5-d]pyrimidine compounds, their use as medicaments, compositions containing them and processes for their preparation.

Platelet adhesion and aggregation are initiating events in arterial thrombosis. Although the process of platelet adhesion to the sub-endothelial surface may have an important role to play in the repair of damaged vessel walls, the platelet aggregation that this initiates can precipitate acute thrombotic occlusion of vital vascular beds, leading to events with high morbidity such as myocardial infarction and unstable angina. The success of interventions used to prevent or alleviate these conditions, such as thrombolysis and angioplasty is also compromised by platelet mediated occlusion or re-occlusion.

A number of converging pathways lead to platelet aggregation. Whatever the initial stimulus, the final common event is a cross linking of platelets by binding of fibrinogen to a membrane binding site, glycoprotein IIb/IIIa (GPIIb/IIIa). The high anti-platelet efficacy of antibodies or antagonists for GPIIb/IIIa is explained by their interference with this final common event. However, this efficacy may also explain the bleeding problems that have been observed with this class of agent. Thrombin can produce platelet aggregation largely independently of other pathways but substantial quantities of thrombin are unlikely to be present without prior activation of platelets by other mechanisms. Thrombin inhibitors such as hirudin are highly effective anti-thrombotic agents, but again may produce excessive bleeding because they function as both anti-platelet and anti-coagulant agents (The TIMI 9a Investigators (1994), *Circulation* 90, pp. 1624–1630; The Global Use of Strategies to Open Occluded Coronary Arteries (GUSTO) IIa Investigators (1994) *Circulation* 90, pp. 1631–1637; Neuhaus K. L. et. al. (1994) *Circulation* 90, pp.1638–1642).

It has been found that ADP acts as a key mediator of thrombosis. A pivotal role for ADP is supported by the fact that other agents, such as adrenaline and 5-hydroxytryptamine (5HT, serotonin) will only produce aggregation in the presence of ADP. The limited anti-thrombotic efficacy of aspirin may reflect the fact that it blocks only one source of ADP which is that released in a thromboxane-dependent manner following platelet adhesion (see e.g. Antiplatelet Trialists' Collaboration (1994), *Br. Med. J.* 308, pp. 81–106; Antiplatelet Trialists' Collaboration (1994), *Br. Med. J.* 308, pp.159–168). Aspirin has no effect on aggregation produced by other sources of ADP, such as damaged cells or ADP released under conditions of turbulent blood flow. ADP-induced platelet aggregation is mediated by the $P_{2T}$-receptor subtype uniquely located on the platelet membrane. Recently it has been shown that antagonists at this receptor offer significant improvements over other anti-thrombotic agents. Accordingly there is a need to find $P_{2T}$-antagonists as anti-thrombotic agents.

It has now been found that a series of triazolo[4,5-d]pyrimidine derivatives are $P_{2T}$-receptor antagonists. In a first aspect the invention therefore provides a compound of formula (I):

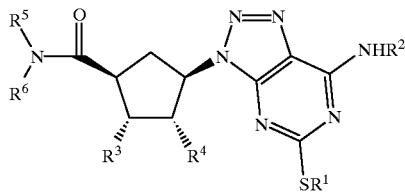

wherein:

$R^1$ is a $C_{1-6}$ alkyl, $C_{2-6}$ alkenyl, $C_{2-6}$ alkynyl, $C_{3-8}$-cycloalkyl, aryl or a thienyl group, each group being optionally substituted by one or more substituents selected from halogen, $OR^8$, $NR^9R^{10}$, $SR^{11}$ or $C_{1-6}$ alkyl (itself optionally substituted by one or more halogen atoms); $R^2$ is $C_{1-8}$ alkyl, $C_{2-8}$ alkenyl or $C_{3-8}$ cycloalkyl each of which may be optionally substituted by one or more substituents selected from halogen, $OR^8$, $NR^9R^{10}$, $SR^{11}$, $C_{1-6}$ alkyl, $C_{3-8}$ cycloalkyl, pyridyl or aryl (the latter two of which may be optionally substituted by one or more substitutents selected from halogen, $OR^{20}$, $C(O)R^{11}$, $NR^{14}C(O)R^{15}$, $NR^{16}SO_2R^{17}$, $SO_2NR^{18}R^{19}$, nitro, $NR^{12}R^{13}$, $SR^{11}$, methylenedioxy or $C_{1-6}$ alkyl which is optionally substituted by one or more halogen atoms);

$R^3$ and $R^4$ are both hydroxy;

$R^5$ is hydrogen or $C_{1-6}$ alkyl; $R^6$ is $C_{1-6}$ alkyl, optionally substituted by one or more groups selected from $C_{1-6}$ alkyl, $C_{2-6}$ alkenyl, $C_{2-6}$ alkynyl, halogen, $OR^{21}$, $C_{3-6}$ cycloalkyl, or $R^6$ is $C_{3-6}$ cycloalkyl, or $R^6$ is —A-phenyl or —A-pyridyl each of which may be optionally substituted by one or more groups selected from $C_{1-6}$ alkyl, $C_{2-6}$ alkenyl, $C_{2-6}$ alkynyl, halogen, $OC_{1-6}$ alkyl, $C_{3-6}$ cycloalkyl, or methylenedioxy; or $R^5$ $R^6$ together with the nitrogen atom to which they are attached for a 5 to 7-membered saturated ring optionally substituted by $C_{1-6}$ alkyl;

A is a bond or $C_{1-6}$ alkyl;

$R^8$ is hydrogen, $C_{1-6}$ alkyl (which may be optionally substituted by one or more halogen atoms) or aryl (which may be optionally substituted by one or more substituents selected from halogen, nitro, $C(O)R^{11}$, $OR^{20}$, $SR^{11}$, $NR^{12}R^{13}$, $NR^{14}C(O)R^{15}$, $NR^{16}SO2R^{17}$, $SO2NR^{18}R^{19}$);

$R^9$ is hydrogen, $C_{1-6}$ alkyl (which may be optionally substituted by one or more halogen atoms) or aryl (which may be optionally substituted by one or more substituents selected from halogen, nitro, $C(O)R^{20}$, $OR^{20}$, $SR^{11}$, $NR^{12}R^{13}$, $NR^{14}C(O)R^{15}$, $NR^{16}SO_2R^{17}$, $SO_2NR^{18}R^{19}$);

$R^{10}$ is hydrogen, $C_{1-6}$ alkyl or $C(O)C_{1-6}$ alkyl;

$R^{12}$ and $R^{13}$ are independently hydrogen, $C_{1-6}$ alkyl or together with the nitrogen atom to which they are attached form a 4- to 8-membered ring;

$R^{15}$ is $C_{1-6}$ alkyl or phenyl;

$R^{11}$, $R^{14}$ and $R^{16}$ are independently hydrogen or $C_{1-6}$ alkyl;

$R^{17}$ is $C_{1-6}$ alkyl or phenyl;

$R^{18}$ and $R^{19}$ are independently hydrogen, $C_{1-6}$ alkyl or phenyl;

$R^{20}$ is hydrogen, phenyl or $C_{1-6}$ alkyl (which may be optionally substituted by halogen);

$R^{21}$ is hydrogen or $C_{1-6}$ alkyl, provided that when $R^{21}$ is H, $R^5$ must be $C_{1-6}$ alkyl. or a pharmaceutically acceptable salt or solvate thereof.

Alkyl groups, whether alone or as part of another group, can be straight chained or branched. Aryl groups include phenyl and naphthyl groups. Acyl groups include $C(O)C_{1-6}$alkyl such as acetyl and 1-oxopropyl.

Suitably $R^1$ is $C_{1-6}$ alkyl, $C_{2-6}$ alkenyl, $C_{2-6}$ alkynyl, $C_{3-8}$-cycloalkyl, aryl or a thienyl group, each group being optionally substituted by one or more substituents selected from halogen, $OR^8$, $NR^9R^{10}$, $SR^{11}$ or $C_{1-6}$ alkyl (itself optionally substituted by one or more halogen atoms). Preferably $R^1$ is $C_{1-6}$ alkyl, thienyl, or trifluoromethylphenyl. More preferably $R^1$ is methyl, propyl, propenyl or thienyl.

Suitably $R^2$ is $C_{1-8}$ alkyl, $C_{2-8}$ alkenyl or $C_{3-8}$ cycloalkyl each of which may be optionally substituted by one or more substituents selected from halogen, $OR^8$, $NR^9R^{10}$, $SR^{11}$, $C_{1-6}$ alkyl, $C_{3-8}$ cycloalkyl, pyridyl or aryl (the latter two of which may be optionally substituted by one or more substituents selected from halogen, $OR^{20}$, $C(O)R^{11}$, $NR^{14}C(O)R^{15}$, $NR^{16}SO_2R^{17}$, $SO_2NR^{18}R^{19}$, nitro, $NR^{12}R^{13}$, $SR^{11}$, methylenedioxy or $C_{1-6}$ alkyl which is optionally substituted by one or more halogen atoms); where $R^8, R^9, R^{10}, R^{11}, R^{14}, R^{15}, R^{16}, R^{17}, R^{18}$ and $R^{19}$ are as defined above. Preferably $R^2$ is $C_{1-6}$ alkyl or a $C_{3-8}$-cycloalkyl group optionally substituted by phenyl which itself can be optionally substituted by halogen, $OR^8$ or $C_{1-6}$-alkyl. More preferably $R^2$ is cyclopropyl optionally substituted by phenyl, 4-methoxyphenyl, 3-chlorophenyl, 4-methylphenyl or 4-fluorophenyl.

Suitably $R^5$ is hydrogen or $C_{1-6}$ alkyl; $R^6$ is $C_{1-6}$ alkyl, optionally substituted by one or more groups selected from $C_{1-6}$ alkyl, $C_{2-6}$ alkenyl, $C_{2-6}$ alkynyl, halogen, $OR^{21}$, $C_{3-6}$ cycloalkyl, or $R^6$ is $C_{3-6}$ cycloalkyl, or $R^6$ is -A-phenyl or -A-pyridyl each of which may be optionally substituted by one or more groups selected from $C_{1-6}$ alkyl, $C_{2-6}$ alkenyl, $C_{2-6}$ alkynyl, halogen, $OC_{1-6}$ alkyl, $C_{3-6}$ cycloalkyl, or methylenedioxy; or $R^5$ and $R^6$ together with the nitrogen atom to which they are attached for a 5 to 7-membered saturated ring optionally substituted by $C_{1-6}$ alkyl. Preferably $R^5$ is hydrogen and $R^6$ is cyclopropyl, methylcyclopropyl, $C_{1-6}$ alkyl, $C_{1-6}$ alkyl substituted by halogen, preferably one or more flouoro atoms. More preferably $R^5$ is ethyl, isopropyl or isobutyl, or $R^5$ and $R^6$ together with the nitrogen atom to which they are attached form a pyrrolidine ring. Most preferably $R^5$ is hydrogen and $R^6$ is methyl or 2-fluoroethyl.

Particularly preferred compounds of the invention include those exemplified herein, both in free base form and as a pharmaceutically acceptable salt or solvate thereof.

According to the invention there is further provided a process for the preparation of a compound of formula (I) which comprises reaction of a compound of formula (II):

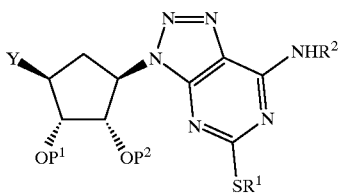

(II)

where $R^1$ and $R^2$ are as defined in formula (I) or are protected derivatives thereof, $P^1$ and $P^2$ are hydrogen or protecting groups and Y is $CO_2H$, with a compound of formula (III):

 (III)

where $R^5$ and $R^6$ are as defined in formula (I), and optionally thereafter in any order:

converting one or more functional groups into a further functional groups removing any protecting groups forming a pharmaceutically acceptable salt or solvate.

Examples of suitable groups which each $P^1$ and $P^2$ can independently represent are $C_{1-6}$-alkyl (preferably methyl), benzyl, $(C_{1-6}$-alkyl$)_3$Si (preferably trimethylsilyl) and a $C(O)C_{1-6}$-alkyl group (preferably acetyl). Preferably the two groups $P^1$ and $P^2$ together with the atoms to which they are attached complete a ring, for example the two groups $P^1$ and $P^2$ together represent an alkylidene such as methylidene or, more preferably, isopropylidene, or an alkoxy methylidene such as ethoxymethylidene.

The reaction of compounds of formula (II) and (III) is preferably carried out in the presence of a coupling agent using methods known from peptide synthesis (see M. Bodanszky and A. Bodanszky, The Practice of Peptide Synthesis, Springer-Verlag, 1984). Suitable coupling agents include 1,1'-carbonyldiimidazole and dicyclohexylcarbodiimide; the preferred coupling agent is bromo-tris-pyrrolidino-phosphonium hexafluorophosphate or benzotriazole-1-yl-oxy-tris-(dimethylamino) phosphoniumhexafluorophosphate, used in the presence of N,N-diiisopropylethylamine. The reaction is preferably carried out in N,N-dimethylformamide (DMF) or tetrahydrofuran THF) and preferably at a temperature of from −15° to 120° C., more preferably at a temperature of from 0° C. to room temperature.

Protecting groups can be added and removed using known reaction conditions. The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Alternative methods of activating a compound of formula (II) wherein Y is $CO_2H$ include formation of an acyl halide or an acetic anhydride. Acid anhydrides may be formed by treatment with an acyl halide, such as acetyl chloride in the presence of a base, such as pyridine or by treatment with a dehydrating agent such as acetic acid anhydride or phosphorus pentoxide in an inert solvent. Acyl halides may be formed by treatment of the acid with a halogenating agent, for example P(III), P(V) or S(IV) halides such as phosphorus trichloride. Acyl halides may also be prepared by an exchange reaction of the acid with an acyl halide such as oxalyl bromide. The reactions may be performed in the halogenating agent or acyl halide as solvent or in other inert solvents such as methylene chloride, at a temperature of from 0 to 150° C. Activation is preferably carried out by treatment with oxalyl chloride in dichloromethane at room temperature.

Deprotection can be carried out using methods generally known in the art. For example for groups $P^1/P^2$ deprotection is preferably carried out as follows:

(i) where one or both of $P^1$ and $P^2$ represent $C(O)C_{1-6}$-alkyl, these groups can be removed by basic hydrolysis, for example by using a metal hydroxide, preferably an alkali metal hydroxide, such as sodium hydroxide or lithium hydroxide, or quaternary ammonium hydroxide in a solvent, such as aqueous ethanol or aqueous tetrahydrofuran, at a temperature of from 10° to 100° C., preferably the temperature is around room temperature; or by acidic hydrolysis using a mineral acid such as HCl or a strong organic acid such as trichloroacetic acid in a solvent such as aqueous 1,4-dioxane;

(ii) where one or both of $P^1$ and $P^2$ represent $(C_{1-6}\text{-alkyl})_3Si$, these can be removed by the use of, for example, a fluoride ion source, for example tetra-n-butylammonium fluoride or hydrogen fluoride;

(iii) where one or both of $P^1$ and $p^2$ represent a $C_{1-6}$-alkyl group, these groups can be removed by the use of, for example, boron tribromide;

(iv) where one or both of $P^1$ and $p^2$ represent a benzyl group these can be removed by hydrogenolysis using a transition metal catalyst, for example palladium on charcoal, under an atmosphere of hydrogen, at a pressure of from 1 to 5 bar, in a solvent, such as acetic acid; and/or (v) where both $P^1$ and $P^2$ together represent alkylidene or an alkoxy alkylidene, they can be removed by the use of, for example, a mineral or organic acid, preferably by using 2M aqueous hydrochloric acid in methanol/1,4-dioxane at room temperature.

Compounds of formula (III) are commercially available or can be prepared by literature methods known to those skilled in the art.

A compound of formula (II) wherein Y is $CO_2H$, $CONR^5R^6$ or $CO_2R'$ can be prepared by reacting a compound of formula (IV):

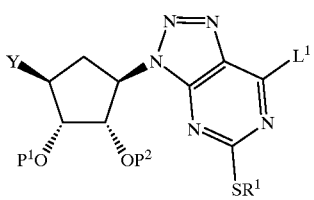

(IV)

wherein $R^1$, $P^1$, $P^2$ $R^5$ and $R^6$ are as defined above, $L^1$ is a leaving group, for example a halogen atom and R' is a $C_{1-6}$-alkyl or benzyl group, with an amine $NH_2R^2$ or a salt of $NH_2R^2$ wherein $R^2$ is as defined above, in the presence of a base. Suitable salts of $NH_2R^2$ include hydrochlorides. Suitable bases include an organic base such as triethylamine or an inorganic base such as potassium carbonate. The amines $NH_2R^2$ can be prepared using procedures described in H Nishiyama etal, Bull. Chem. Soc., Jpn., 1995, 68, 1247, P. Newman, Optical Resolution Procedures for Chemical Compounds, Vol. 1, Amines and Related Compounds; Optical Resolution and Information Centre: Manhattan College, Riverdale, N.Y., 1978, p120, J. Vallgarda etal, J. Chem. Soc. Perkin 1, 1994, 461. Certain amines $NH_2R^2$ are novel compounds and form a further aspect of the invention.

A compound of formula (IV) can be prepared by diazotising a compound of formula (V):

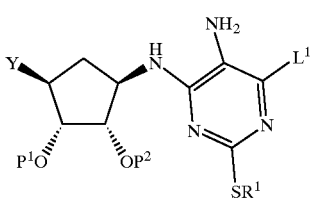

(V)

wherein $R^1$, Y, $L^1$, $P^1$ and $P^2$ are as defined above, with a metal nitrite, for example an alkali metal nitrite, especially sodium nitrite in dilute aqueous acid, for example 2M HCl, or with a $C_{1-6}$-alkyl nitrite in an inert solvent, at a temperature of from −20 to 100° C.; preferred conditions are isoamyl nitrite in acetonitrile at 80° C.

A compound of formula (V) where Y is $CO_2H$ can be prepared by reducing and hydrolysing a compound of formula (VI):

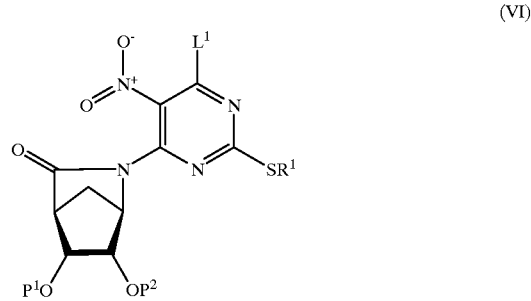

(VI)

wherein $R^1$, $L^1$, $P^1$ and $P^2$ are as defined above. The reduction may be carried for example by using hydrogenation with a transition metal catalyst at a temperature around room temperature, for example palladium on charcoal under an atmosphere of hydrogen, preferably at a pressure from 1 to 5 atmospheres, in a solvent, for example ethanol, or by using iron in an acidic solvent such as acetic acid at a temperature of about 100° C.

To prepare a compound of formula (V) wherein Y is $CO_2H$, following the above reaction, hydrolysis of the compound derived from the compound of formula (VI) may be performed by using a mineral acid such as HCl or a strong organic acid such as trifluoroacetic acid in a solvent such as aqueous 1,4-dioxane, at a temperature of from 20 to 150° C. Preferably the reduction and hydrolysis are carried out simultaneously using iron in an acidic solvent for example acetic acid, containing an alkaline earth metal halide, for example calcium chloride, at a temperature of about 80° C.

To prepare a compound of formula (V) wherein $R^9$ is $C_{1-6}$-alkyl or benzyl, the compound of formula (VI) is treated with iron in acetic acid at a temperature of from 50 to 80° C. so that the nitro group is reduced. The resulting intermediate is then treated with sodium borohydride in a mixture of water and $C_{1-6}$-alkyl alcohol or benzyl alcohol at around room temperature.

A compound of formula (VI) can be prepared by reacting a compound of formula (VII):

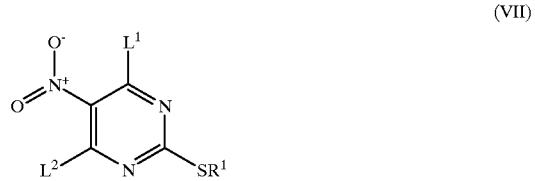

(VII)

wherein $L^1$ and $R^1$ are as defined above and $L^2$ is a leaving group, for example a halogen atom, wherein $L^1$ and $L^2$ are preferably the same, with a compound of formula (VIII):

(VIII)

wherein $P^1$ is as defined above, in the presence of a base such as $C_{1-6}$-alkyl-M or MH wherein M is a metal, for example butyl lithium, in an inert solvent, such as tetrahydrofuran (THF), at a temperature of from −10 to 100° C. Preferably sodium hydride is used in THF at room temperature.

A compound of formula (VII) may be prepared from 4,6-dihydroxy-2-mercaptopyrimidine by alkylation with $R^1L^3$ wherein $R^1$ is as defined above and $L^3$ is a suitable leaving group, for example a halogen atom, followed by nitration, whereafter the two alcohols are is converted to leaving groups $L^1$ and $L^2$.

A compound of formula (V) where Y is $CONR^5R^6$ can be prepared by reacting a compound of formula (IX):

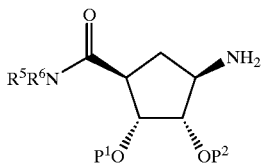

(IX)

with a compound of formula (VII) where $P^1$, $P^2$, $R^1$, $R^5$, $R^6$, $L^1$, and $L^2$ are as defined above in a suitable solvent such as 1,4-dioxane in the presence of a base such as N,N-diisopropylethylamine followed by reduction of the nitro group. Compounds of formula (IX) may be prepared using procedures described in WO9528160.

The group $SR^1$ can be interconverted by oxidation of the sulphur, for example using oxone® or mCPBA, followed by treatment with a compound $R^1SM$ where $R^1$ is a different R group and M is a metal such as sodium.

All novel intermediates form a further aspect of the invention.

Salts of the compounds of formula (I) may be formed by reacting the free acid, or a salt thereof, or the free base, or a salt or a derivative thereof, with one or more equivalents of the appropriate base (for example ammonium hydroxide optionally substituted by $C_{1-6}$-alkyl or an alkali metal or alkaline earth metal hydroxide) or acid (for example a hydrohalic (especially HCl), sulphuric, oxalic or phosphoric acid). The reaction may be carried out in a solvent or medium in which the salt is insoluble or in a solvent in which the salt is soluble, e.g. water, ethanol, THF or diethyl ether, which may be removed in vacuo, or by freeze drying. The reaction may also be a metathetical process or it may be carried out on an ion exchange resin. The non-toxic physiologically acceptable salts are preferred, although other salts may be useful, e.g. in isolating or purifying the product.

The compounds of the invention act as $P_{2T}$-receptor antagonists. Accordingly, the compounds are useful in therapy, especially adjunctive therapy, particularly they are indicated for use as: inhibitors of platelet activation, aggregation and degranulation, anti-thrombotic agents or in the treatment or prophylaxis of unstable angina, coronary angioplasty (PTCA), myocardial infarction, perithrombolysis, primary arterial thrombotic complications of atherosclerosis such as thrombotic or embolic stroke, peripheral vascular disease, myocardial infarction with or without thrombolysis, arterial complications due to interventions in atherosclerotic disease such as angioplasty, endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardiopulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, atheromatous plaque formation/progression, vascular stenosis/restenosis and asthma, in which platelet-derived factors are implicated in the disease process.

According to the invention there is further provided the use of a compound according to the invention in the manufacture of a medicament for the treatment of the above disorders. The invention also provides a method of treatment of the above disorders which comprises administering to a patient suffering from such a disorder a therapeutically effective amount of a compound according to the invention.

The compounds may be administered topically, e.g. to the lung and/or the airways, in the form of solutions, suspensions, HFA aerosols and dry powder formulations; or systemically, e.g. by oral administration in the form of tablets, pills, capsules, syrups, powders or granules, or by parenteral administration in the form of sterile parenteral solutions or suspensions, by subcutaneous administration, or by rectal administration in the form of suppositories or transdermally.

The compounds of the invention may be administered on their own or as a pharmaceutical composition comprising the compound of the invention in combination with a pharmaceutically acceptable diluent, adjuvant or carrier. Particularly preferred are compositions not containing material capable of causing an adverse, e.g. an allergic, reaction.

Dry powder formulations and pressurized HFA aerosols of the compounds of the invention may be administered by oral or nasal inhalation. For inhalation the compound is desireably finely divided.

The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol or another polyol. Suitable carriers include sugars and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound with or without a carrier substance is delivered to the patient.

The pharmaceutical composition comprising the compound of the invention may conveniently be tablets, pills, capsules, syrups, powders or granules for oral administration; sterile parenteral or subcutaneous solutions, suspensions for parenteral administration or suppositories for rectal administration.

For oral administration the active compound may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet may be coated with a suitable polymer dissolved in either a readily volatile organic solvent or an aqueous solvent.

For the preparation of soft gelatine capsules, the compound may be admixed with e.g. a vegetable oil or polyethylene glycol. Hard gelatine capsules may contain granules of the compound using either the above mentioned excipients for tablets, e.g. lactose, saccharose, sorbitol, mannitol, starches, cellulose derivatives or gelatine. Also liquid or semisolid formulations of the drug may be filled into hard gelatine capsules.

Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in art.

The invention is illustrated by the following examples. In the examples the NMR spectra were measured on a Varian Unity Inova 300 or 400 spectrometer and the MS spectra were measured as follows: EI spectra were obtained on a VG 70-250S or Finnigan Mat Incos-XL spectrometer, APCI spectra were obtained on Finnigan Mat SSQ7000 or a Micromass Platform spectrometer. Preparative HPLC separations were generally performed using a Novapak®, Bondapak® or Hypersil® column packed with BDSC-18 reverse phase silica. Flash chromatography (indicated in the Examples as ($SiO_2$)) was carried out using Fisher Matrix silica, 35–70 $\mu$m.

For examples which show the presence of rotamers in proton NMR spectra only the chemical shifts of the major rotamer are quoted.

EXAMPLE 1

[1S-[1α,2β,3β,4α(1S*,2R*)]]-N-Ethyl-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide a) [3aR-(3aα,4α,6α,6aα)]-6-[[5-Amino-6-chloro-2-(propylthio)-4-pyrimidinyl]amino]-tetrahydro-2,2-dimethyl-4H-cyclopenta-1,3-dioxole-4-carboxylic acid Iron powder (10.0 g) was added to a stirred solution of [3aS-(3aα,4β,7β,7aα)]5-[6-chloro-5-nitro-2-(propylthio) pyrimidin-4-yl]-tetrahydro-2,2-dimethyl-4,7-methano-1,3-dioxolo[4,5-c]pyridin-6(3aH)-one (10.0 g) (prepared as described in WO9703084), and calcium chloride in ethanol (140 ml). The reaction mixture was heated at reflux for 10 minutes then filtered through celite, washing several times with hot ethanol. The filtrate was concentrated to afford the desired product (9.3 g).

MS (FAB) 405, 403 (M+H⁺), 403 (100%).

b) [3aR-(3aα,4α,6α,6aα)]-6-[7-Chloro-5-(propylthio)-3H-1,2,3-triazolo[4,5-d]pyrimidin-3-yl]-tetrahydro-2,2-dimethyl-4H-cyclopenta-1,3-dioxole-4-carboxylic acid Isoamyl nitrite (6.02 ml) was added to a solution of the product of step a) (9.28 g) in acetonitrile (80 ml) and the solution heated at 70° C. for 1 hour. The cooled reaction mixture was concentrated and purified ($SiO_2$, ethyl acetate:isohexane 2:1 as eluant) to afford the subtitle compound (7.9 g).

MS (FAB) 416, 414 (M+H⁺), 414 (100%).

c) [3aR-[3aα,4α,6α(1R*,2S*),6aα]]-Tetrahydro-2,2ethyl-6-[7-(2-phenylcyclopropylamino)-5-(propylthio)-3H-1,2,3-triazolo[4,5-d]pyrimidin-3-yl]4H-cyclopenta-1,3-dioxole-4-carboxylic acid A mixture of the product of step b) (413 mg), (1R-trans)-2-phenylcyclopropylamine [R-(R*,R*)]-2,3-dihydroxybutanedioate (1:1) (Prepared as described by L. A. Mitscher et al, J. Med. Chem., 1986, 29, 2044) (283 mg) and triethylamine (1.1 ml) in dichloromethane (6 ml) was stirred at room temperature for 4 hours. The reaction mixture was concentrated and the residue purified ($SiO_2$, ethyl acetate then methanol:ethyl acetate 1:4 as eluant) to afford the subtitle compound (390 mg).

MS (APCI) 511 (M+H⁺, 100%).

d) [3aR-[3aα,4α,6α,6aα(1R*,2S*)]]-N-Ethyl-tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxamide N,N-Diisopropylethylamine (0.5 ml) was added to a solution of ethylamine (70% in water) (5 ml), bromo-tris-pyrrolidino-phosphonium hexafluorophosphate (0.56 g) and the product of step c) (0.51 g) in THF (20 ml). The reaction mixture was stirred at room temperature for 2 hours then concentrated. Chromatography ($SiO_2$, ethyl acetate: dichloromethane 1:2 as eluant) gave the subtitle compound (0.48 g).

MS (APCI) 538 (M+H⁺, 100%).

e) [1S-[1α,2β,3β,4α(1S*,2R*)]]-N-Ethyl-2,3dihydroxy-4-[7-[(2-phenylcyclopropyl)amino]-5-(propylthio)-3H-1,2,3-triazolo[4,5-d]pyrimidin-3-yl]-cyclopentanecarboxamide A solution of the product from step d) (0.47 g) in methanol (16 ml), 1,4-dioxane (4 ml) and 2M aqueous hydrochloric acid (5 ml) was stirred at room temperature for 2 hours. The reaction mixture was concentrated and the residue taken into ethyl acetate (50 ml) and washed with water (2×50 ml). The organic phase was dried and concentrated. The resulting solid was recrystallised (ethyl acetate, 25 ml) to afford the title compound (0.25 g).

Mpt 177–178° C.

MS (APCI) 498 (M+H⁺, 100%).

NMR δH (d₆-DMSO) 9.35 (1H, d), 7.92 (1H, t), 7.31–7.15 (5H, m), 5.13 (1H, d), 4.96 (2H, m), 4.43 (1H, m), 4.11 (1H, m), 3.19 (1H, m), 3.11 (2H, m), 3.00–2.80 (2H, m), 275 (1H, m), 2.40–2.20 (2H, m), 2.13 (1H, m), 1.52 (3H, m), 1.35 (1H, m), 1.04 (3H, t), 0.80 (3H, t).

EXAMPLE 2

[1S-[1α,2β,3β,4α(1S*,2R*)]]-2,3-Dihydroxy-N-(1-methylethyl)-4-[7-((2-phenylcyclopropyl)amino-5-(propylthio)-3H-1,2,3-triazolo[4,5-d]pyrimidin-3-yl]-cyclopentanecarboxamide a) [3aR-[3aα,4α,6α(1R*,2S*),6aα]]-Tetrahydro-2,2-dimethyl-N-(1-methylethyl)-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxamide The subtitle compound was prepared according to the method of example 1, step d) using 1-methylethylamine.

MS (APCI) 552 (M+H⁺, 100%).

b) [1S-[1α,2β,3β, 4α(1S*,2R*)]]-2,3-Dihydroxy-N-(1-methylethyl)-4-[7-[(2-phenylcyclopropyl)amino]-5-(propylthio)-3H-1,2,3-triazolo[4,5-d]pyrimidin-3-yl]-cyclopentanecarboxamide The title compound was prepared according to the method of example 1 step e) using the product of step a).

Mpt 179–181° C.

MS (APCI) 512 (M+H⁺, 100%).

NMR δH (d₆-DMSO) 9.35 (1H, d), 7.82 (1H, t), 7.31–7.16 (5H, m), 4.96 (2H, m), 4.43 (1H, m), 4.10 (1H, m), 3.85 (1H, q), 3.19 (1H, m), 3.00–2.80 (2H, m), 2.75 (1H, m), 2.40–2.20 (2H, m), 2.13 (1H, m), 1.52 (3H, m), 1.35 (1H, m), 1.24 (6H, m), 0.80 (3H, t).

EXAMPLE 3

[1S-[1α,2β,3β, 4α(1S*,2R*)]]-2,3-Dihydroxy-N-(2-methylpropyl)-4-[7-[(2-phenylcyclopropyl)amino]-5-(propylthio)-3H-1,2,3-triazolo[4,5-d]pyrimidin-3-yl]-cyclopentanecarboxamide a) [3aR-[3aα,4α,6α(1R*,2S*),6aα]]-Tetrahydro-2,2-dimethyl-N-(2-methylpropyl)-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxamide The subtitle compound was prepared according to the method of example 1 step d), using 2-methylpropylamine.

MS (APCI) 566 (M+H⁺, 100%).

b) [1S-[1α,2β,3β,4α(1S*,2R*)]]-2,3-Dihydroxy-N-(2-methylpropyl)-4-[7-[(2-phenylcyclopropyl)amino]-5-(propylthio)-3H-1,2,3-triazolo[4,5-d]pyrimidin-3-yl]-cyclopentanecarboxamide The title compound was prepared according to the method of example 1 step e) using the product of step a).

Mpt 191–193° C.

MS (APCI) 526 (M+H⁺, 100%).

NMR δH (d₆-DMSO) 9.36 (1H, d), 7.88 (1H, t), 7.31–7.15 (5H, m), 5.14 (1H,d), 4.98 (2H, m), 4.44 (1H, m), 4.13 (1H, m), 3.19 (1H, m), 2.96–2.75 (4H, m), 2.49–2.20 (2H, m), 2.13 (1H, m), 1.71 (1H, m), 1.50 (3H m), 1.35(1H, m), 0.85 (6H, d), 0.81 (3H, t).

EXAMPLE 4

[1S-[1α,2β,3β,4α(1S*,2R*)]]-N-Ethyl-2,3-dihydroxy-4-[5-(-methylethylthio)-7-[(2-phenylcyclopropyl)amino]-3H-1,2,3-triazolo[4,5-d]pyrimidin-3-yl]-cyclopentanecarboxamide a) [1S-[1α,2β,3β,4α(1S*,2R*)]]-N-Ethyl-2,3-dihydroxy-4-[7-[(2-phenylcyclopropyl)amino]-5-(propylsulphonyl)-3H-1,2,3-triazolo[4,5-d]pyrimidin-3-yl]-cyclopentanecarboxamide 3-Chloroperoxybenzoic acid (50%, 9.0 g) was added to a suspension of the product of example 1, step e) (4.1 g) in ethanol (200 ml) and dichloromethane (50 ml) and the resulting solution stirred at room temperature for 18 hours. The reaction mixture was concentrated and the residue taken up in ethyl acetate (500 ml), washed with 10% aqueous sodium metabisulfite solution (2×100 ml) and 10% aqueous sodium bicarbonate solution (2×100 ml) then dried and concentrated. Purification (SiO₂, ethyl acetate as eluant) gave the subtitle compound (2.4 g).

Mpt 203–207° C.

MS (APCI) 530 (M+H⁺, 100%).

b) [1S-[1α,2β,3β,4α(1S*,2R*)]]-N-Ethyl-2,3-dihydroxy-4-[5-(1-methylethylthio)-7-[(2-phenylcyclopropyl)amino]-3H-1,2,3-triazolo[4,5-d]pyrimidin-3-yl]-cyclopentanecarboxamide Propane-2-thiol (0.23 g) was added dropwise to a suspension of sodium hydride (60%, 120 mg) in dimethylformamide (DMF) (10 ml). After 30 minutes, the product of step a) (0.40 g) was added portionwise over 10 minutes then the reaction stirred for 2 hours. The reaction mixture was added slowly to a saturated aqueous solution of sodium chloride (20 ml), then the solution extracted with ethyl acetate (2×50 ml). The organic phase was dried and concentrated and the residue purified by HPLC (Novapak®, C18 column 0.1% aqueous ammonium acetate:acetonitrile, gradient elution 70:30 to 0:100 over 15 minutes) to give the title compound (0.23 g).

Mpt 160–161° C.

MS (APCI) 498 (M+H⁺, 100%).

NMR δH (d₆-DMSO) 9.38 (1H, d), 7.91 (1H, m), 7.31–7.16 (5H, m), 5.12 (1H, d), 4.99 (2H, m), 4.42 (1H, m), 4.10 (1H, m), 3.62 (1H, m), 3.19 (1H, m), 3.10 (2H, m), 2.72 (1H, m), 2.40–2.20 (2H, m), 2.10 (1H, m), 1.58 (1H, m), 1.38 (1H, m), 1.21–0.98 (9H, m).

EXAMPLE 5

[1S-[1α,2β,3β,4α(1S*,2R*)]]-N-Ethyl-2,3-dihydroxy-4-[7-[(2-phenylcyclopropyl)amino]-5-[4-(trifluoromethyl)phenylthio]-3H-1,2,3-triazolo[4,5-d]pyrimidin-3-yl]-cyclopentanecarboxamide The title compound was prepared according to the method of example 4 step b), using 4-(trifluoromethyl)thiophenol Mpt 202–203° C.

MS (APCI) 600 (M+H⁺, 100%).

NMR δH (d₆-DMSO) 9.45 (1H, d), 7.93 (1H, m), 7.79 (2H,d), 7.60 (2H, d), 7.30–7.08 (5H, m), 5.13 (1H, d), 4.96 (1H, d), 4.90 (1H, m), 4.40 (1H, m), 4.02 (1H, m), 3.10 (3H, m), 2.70 (1H, m), 2.32–2.19 (3H, m), 1.40 (1H, m), 1.15 (1H, m), 1.03 (3H, t).

EXAMPLE 6

[1S-[1α,2β,3β,4α(1S*,2R*)]]-N-Ethyl-2,3-dihydroxy-4-[7-[(2-phenylcyclopropyl)amino]-5-(thien-2-ylthio)-3H-1,2,3-triazolo[4,5-d]pyrimidin-3-yl]-cyclopentanecarboxamide The title compound was prepared according to the method of example 4 step b), using thiophene-2-thiol.

Mpt 198–200° C.

MS (APCI) 538 (M+H, 100%).

NMR δH (d₆-DMSO) 9.43 (1H, d), 7.92 (1H, m), 7.69 (1H, d), 7.67–7.02 (7H, m), 5.12 (1H, d), 4.95 (1H, d), 4.82 (1H, m), 4.38 (1H, m), 4.05 (1H, m), 3.20 (1H, m), 3.10 (2H, m), 2.71(1H, m), 2.32–2.10 (3H, m), 1.43 (1H, m), 1.19 (1H, m), 1.02 (3H, t).

EXAMPLE 7

[1S-[1α,2β,3β,4α(1S*,2R*)]]-N-Ethyl-2,3-dihydroxy-4-[7-[[2-(4-methoxyphenyl)cyclopropyl]amino]-5-(propylthio)-3H-1,2,3-txiazolo[4,5-d]pyrimidin-3-yl]-cyclopentanecarboxamide a) (1R-trans)-2-(4-Methoxyphenyl)cyclopropane carboxylic acid To a solution of dichloro(p-cymene)ruthenium (II) dimer (250 mg) and 2,6-bis[(4S)isopropyl-2-oxazolin-2-yl] pyridine (240 mg) in dichloromethane (150 ml) was added 1-methoxy-4-vinylbenzene (25 g). To this solution was added ethyl diazoacetate (5.0 g) in dichloromethane (20 ml) over 6 hours. The solution was maintained at room temperature for 18 hours then diluted with i-hexane (200 ml) and passed through a plug of silica (50 g) washing with i-hexane/dichloromethane (1:1, 250 ml). The filtrate was concentrated and the residue taken into methanol (100 ml). Lithium hydroxide (4.0 g) in water (10 ml) was added and the mixture heated at reflux for 4 hours. The resulting solution was concentrated to give a solid which was washed with 1:1 ether/i-hexane (100 ml). The solid was then triturated with 2N HCl and the white precipitate collected to give the subtitle compound (5.1 g).

MS (APCI) 191 (M–H, 100%)

b) (1R-trans)-2-(4-Methoxyphenyl)cyclopropanamine, [R-(R*,R*)]-2,3-dihydroxybutanedioate (1:1)

To a solution of the product from step a (1.0 g) and triethylamine (608 mg) in acetone /water (4:1, 50 ml) at 0° C. was added ethyl chloroformate (648 mg) over 5 minutes. The solution was maintained at 0° C. for 30 minutes before addition of sodium azide (428 mg) in water (10 ml). After a further 30 minutes, water (100 ml) was added and the reaction mixture extracted with toluene (2×100 ml). The organic extracts were combined and dried, then heated at reflux for 4 hours behind a blast screen. The solution was concentrated and the residue dissolved in 1,4-dioxane (25 ml) and 6N HCl (25 ml) added. The solution was heated at 80° C. for 3 hours, then the aqueous phase was basified with 2N sodium hydroxide solution. The aqueous solution was extracted with dichloromethane (3×50 ml) which was dried and concentrated. This residue was taken into ethanol (5 ml) and L-tartaric acid (750 mg) in ethanol (5 ml) added. The resulting solid was collected and recrystallised (isopropyl alcohol:water 3:1) to afford the subtitle compound as colourless needles (1.32 g).

mpt 192–3° C.

NMR δH (d$_6$-DMSO) 7.05 (2H, d), 6.85 (2H, d), 3.91 (2H, s), 3.71 (3H, s), 2.70–2.60 (1H, m), 2.15–2.07 (1H, m), 1.22–1.08 (1H, m), 1.03 (1H, dd).

c) [3aR-(3aα,4α,6α,6aα)]-6-[[6-Chloro-5-nitro-2-(propylthio)-4-pyrimidinyl]amino]-N-ethyl-tetrahydro-2,2-dimethyl-4H-cyclopenta-1,3-dioxole-4-carboxamide A solution of 4-amino-N-ethyl-tetrahydro-2,2-dimethyl-4H-cyclopenta-1,3-dioxole-4-carboxamide (14.0 g) (prepared as described in WO 9528160) in 1,4-dioxane (15 ml) was added over 5 minutes to a stirred solution of 3,6-dichloro-5-nitro-2-propylthiopyrimidine (32.9 g) (prepared as described in WO9703084) in 1,4-dioxane at 10° C. N,N-Diisopropylethylamine (16.0 ml) was then added and the mixture allowed to warm to room temperature overnight. The reaction mixture was concentrated and the residue purified (SiO$_2$, ether:isohexane 4:1 as eluant) to afford the subtitle compound (17.3 g).

MS (APCI) 460 (M+H$^+$, 100%).

d) [3aR-(3aα,4α,6α,6aα)]-6-[7-Chloro-5-(propylthio)-3H-1,2,3-triazolo[4,5-d]pyrimidin-3-yl]-N-ethyl-tetrahydro-2,2-dimethyl-4H-cyclopenta-1,3-dioxole-4-carboxamide To a solution of the product from step c) (32.0 g) in acetic acid (300 ml) was added iron powder (40.0 g). The mixture was stirred at room temperature for 2 hours then filtered through celite washing with ethyl acetate (3×150 ml). The filtrate was concentrated to a volume of 150 ml then cooled to 10° C. Sodium nitrite (7.5 g) in water (25 ml) was added and the solution allowed to warm to room temperature over 40 minutes. Water (200 ml) was then added and the resultant precipitate collected by filtration, washing with water (100 ml) and isohexane (100 ml) afforded the subtitle compound (26.4 g).

MS (APCI) 441 (M+H$^+$, 100%).

e) [1S-[1α,2β,3β,4α(1S*,2R*)]]-N-Ethyl -2,3-dihydroxy-4-[7-[[2-(4-methoxyphenyl)cyclopropyl]amino]-5-(propylthio)-3H-1,2,3-triazolo[4,5-d]pyrimidin-3-yl-cyclopentanecarboxamide A mixture of the product of step d) (250 mg) and the product of step b), (156 mg) and N,N-diisopropylethylamine (258 mg) in N,N -dimethylformamide (6 ml) was stirred at room temperature for 24 hours. The reaction mixture was concentrated and the residue dissolved in ethyl acetate (5 ml) and hydrochloric acid solution (2M, 5 ml) added. The reaction was allowed to stand overnight then the resulting crystals collected, washed with ether and dried in vacuo to afford the title compound as colourless needles (125 mg).

Mpt 199–200° C.

MS (APCI) 528 (M+H$^+$, 100%).

NMR δH (d$_6$-DMSO) 9.30 (1H, d), 7.90 (1H, t), 7.13 (2H, d), 6.85 (2H, d), 5.12 (1H, d), 5.00–4.88 (2H, m), 4.45 (1H, dd), 4.10 (1H, dd), 3.74 (3H, s), 3.16–3.05 (3H, m), 3.00–2.80 (2H, m), 2.78–2.69 (1H, m), 2.40–2.18 (2H, m), 2.14–2.06 (1H, m), 1.60–1.40 (2H, m), 2.30–2.20 (1H, m), 1.02 (3H, t), 0.84 (3H, t).

EXAMPLE 8

[1S-[1α,2β,3β,4α(1S*,2R*)]]4-[7-[[2-(3-Chlorophenyl)cyclopropyl]amino]-5-(propylthio)-3H-1,2,3-triazolo[4,5-d]pyrimidin-3-yl]-N-ethyl-2,3-dihydroxy cyclopentanecarboxamide a) (1R-trans)-2-(3-Chlorophenyl)cyclopropanamine Prepared from 3-chloro-1-vinylbenzene according to the method of Example 7 steps a) and b), except that the product was afforded as the free amine.

NMR δH (d$_6$-DMSO) 7.05–1.15 (2H, m), 6.97 (1H, s), 8.89(1H, d), 2.53 (1H, m), 1.80–1.83 (1H, m), 1.10–1.03 (1H, m), 1.00–0.95 (1H, m)

b) [1S-[1α,2β,3β,4α(1S*,2R*)]]4-[7-[[2-(3-Chlorophenyl)cyclopropyl]amino]-5-(propylthio)-3H-1,2,3-triazolo[4,5-d]pyrimidin-3-yl]-N-ethyl-2,3-dihydroxy cyclopentanecarboxamide The title compound was prepared according to the method of example 7 step e), using the product of step a).

Mpt 194–197° C.

MS (APCI) 532 (M+H$^+$, 100%).

NMR δH (d$_6$-DMSO) 9.38 (1H, d), 7.93 (1H, t), 7.31–7.25 (2H, m), 7.23 (1H, d), 7.16 (1H, d), 4.96 (1H, dd), 4.30 (1H, dd), 4.09 (1H, t), 3.22–3.18 (1H, m), 3.15–3.02 (2H, m), 3.00–2.80 (2H, m), 2.80–2.70 (1H, m), 2.40–2.1 (3H, m), 1.60–1.35 (3H, m), 1.02 (3H, m), 1.02 (3H, t), 0.89 (3H, t).

EXAMPLE 9

[1S-[1α,2β,3β,4α(1S*,2R*)]]-N-Ethyl-2,3dihydroxy-4-[7-[[2-(4-methylphenyl)cyclopropyl]amino]-5-(propylthio)-3H-1,2,3-triazolo[4,5-d]pyrimidin-3-yl]-cyclopentanecarboxamide a) (1R-trans)-2-(4-Methylphenyl)cyclopropanamine Prepared from 4-methyl-1-vinylbenzene according to the method of Example 7 steps a) and b), except the product was isolated as the free amine.

NMR δH (d$_6$-DMSO) 7.08 (2H, d), 7.00 (2H, d), 3.98 (2H, s), 2.70 (1H, m), 2.50 (3H, bs), 2.30–2.20 (1H, m), 1.30–1.22 (1H, m), 1.09–1.00 (1H, m)

b) [1S-[1α,2β,3β,4α(1S*,2R*)]]-N-Ethyl-2,3-dihydroxy-4-[7-[[2-(4-methylphenyl)cyclopropyl]amino]-5-(propylthio)-3H-1,2,3-triazolo[4,5-d]pyrimidin-3-yl]-cyclopentanecarboxamide The title compound was prepared according to the method of example 7 step e), using the product of step a).

MS (APCI) 512 (M+H$^+$, 100%).

NMR δH (d$_6$-DMSO) 9.32 (1H, d), 7.91 (1H, t), 7.07 (4H, s), 5.11 (1H, bs), 4.97 (2H, m), 4.29 (1H, bs), 4.10 (1H, bs), 3.20–3.00 (3H, m), 3.00–2.80 (2H, m), 2.78–2.66 (1H, m), 2.40–2.20 (2H, m), 2.30 (3H, s), 2.15–2.02 (1H, m), 1.57–1.40 (2H, m), 1.26 (1H, dd), 1.02 (3H, t), 0.83 (3H, t)

EXAMPLE 10

[1S-[1α,2β,3β,4α(1S*,2R*)]]-N-Ethyl-2,3-dihydroxy-4-[5-(methylthio)-7-[(2-phenylcyclopropyl)amino-3H-1,2,3-triazolo[4,5d]pyrimidin-3-yl]-cyclopentanecarboxamide The title compound was prepared according to the method of example 4 step b), using sodium thiomethoxide.

MS (APCI) 470 (M+H$^+$, 100%).

NMR δH (d$_6$-DMSO) (363K) 9.00 (1H, bs), 7.61 (1H, bs), 7.28 (2H, t), 7.20–7.10 (3H, m), 4.99 (1H, dd), 4.46 (1H, t), 4.18 (1H, t), 3.20–3.10 (2H, m), 2.82–2.71 (1H, m), 2.40 (3H, bs), 2.35–2.20 (4H, m), 1.50–1.40 (1H, m), 1.32 (1H, dd), 1.04 (3H, t).

EXAMPLE 11

[1S-[1α,2β,3β,4α(1S*,2R*)]]-N-Ethyl-2,3-dihydroxy-4-[7-[(2-phenylcyclopropyl)amino]-5-(2-propenylthio)-3H-1,2,3-triazolo[4,5-d]pyrimidin-3-yl]-cyclopentanecarboxamide The title compound was prepared according to the method of example 4 step b), using 2-propenylthiol.

MS (APCI) 496 (M+H$^+$, 100%).

NMR δH (d$_6$-DMSO) 9.39 (1H, d), 7.93 (1H, t), 7.28 (2H, t), 7.17 (3H, m), 5.89–5.80 (1H, m), 5.15–5.07 (2H, m), 5.02–4.93 (3H, m), 4.43 (1H, dd), 3.66 (2H, ddd), 3.20 (1H, m), 3.13–3.05 (2H, m), 2.80–2.70 (1H, m), 2.40–2.10 (3H, m), 1.53–1.48 (1H, m), 1.40–1.30 (1H, m), 1.03 (3H, t).

EXAMPLE 12

1-[[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentylcarbonyl]-pyrrolidine a) 1-[[3aR-(3aα,4α,6α,6aα)]-Tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-carbonyl]-pyrrolidine Prepared according to the method of example 1 step d), using pyrrolidine.

MS (APCI) 562 (M–H$^+$, 100%).

b) 1-[[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-cyclopentylcarbonyl]-pyrrolidine Prepared according to the method of example 1 step e), using the product of step c).

MS (APCI) 562 (M–H$^+$, 100%).

NMR δH (d$_6$-DMSO) 9.33 (1H, d), 7.31–7.27 (2H, m), 7.20–7.16 (3H, m), 5.15 (1H, d), 5.08 (1H, d), 5.02–5.00 (1H, m), 4.44–4.42 (1H, m), 4.14–4.13 (1H, m), 3.64–3.54 (1H, m), 3.51–3.40 (1H, m), 3.25–3.16 (1H, m), 3.10–2.91 (1H, m), 2.90–2.79 (1H, m), 2.36–2.32 (2H, m), 2.17–2.09 (1H, m), 1.90–1.86 (1H, m), 1.80–1.78 (2H, m), 1.53–1.48 (3H, m), 1.48–1.31 (1H, m), 0.81 (3H, t).

EXAMPLE 13

[1S-[1α,2β,3β,4α(1S*,2R*)]]-N-(Cycopropylmethyl)-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide a) [3aR-[3aα,4α,6α(1R*,2S*),6aα]]-N-(Cyclopropymethyl)-tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3dioxole-4-carboxamide The subtitle compound was prepared according to the method of example 1 step d), using cyclopropylmethylamine.

Mpt 208–209° C.

MS (APCI) 564 (M+H$^+$, 100%).

b) [1S-[1α,2β,3β,4α(1S*,2R*)]]-N-(Cyclopropylmethyl)-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide The title compound was prepared according to the method of example 1 step e), using the product of step a).

Mpt 189–191° C.

MS (APCI) 524 (M+H$^+$, 100%).

NMR δH (d$_6$-DMSO) 9.35 (1H, d), 8.01 (1H, t), 7.30–7.19 (5H, m), 5.13 (1H, d), 4.97 (2H, m), 4.44 (1H, m), 4.10 (1H m), 3.21 (1H, m), 2.97 (3H, m), 2.82 (1H, m), 2.79 (1H, m), 2.38–2.20 (2H, m), 2.13 (1H, m), 1.55–1.41 (3H, m), 1.35 (1H, m), 0.89 (1H, m), 0.81 (3H, t), 0.39 (2H, m). 0.16 (2H, m).

EXAMPLE 14

[1S-[1α,2β,3β,4α(1S*,2R*)]]-N-(Cyclopropyl)-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide a) [3aR-[3aα,4α,6α(1R*,2S*),6aα]]-N-(Cyclopropyl)-tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxamide The subtitle compound was prepared according to the method of example 1, step d) using cyclopropylamine.

MS (APCI) 550 (M+H$^+$, 100%).

b) [1S-[1α,2β,3β,4α(1S*,2R*)]]-N-(Cyclopropyl)-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide The title compound was prepared according to the method of example 1 step e), using the product of step a).

Mpt 168–170° C.

MS (APCI) 510 (M+H$^+$, 100%).

NMR δH (d$_6$-DMSO) 9.36 (1H, d), 8.00 (1H, m), 7.30–7.16 (5H, m), 4.95 (1H, m), 4.42 (1H, t), 4.09 (1H, t), 3.20 (1H, m), 2.96–2.82 (2H, m), 2.66 (2H, m), 2.28–2.22 (2H, m), (2H, m), 2.13 (1H, m), 1.51 (3H, m), 1.35 (1H, m), 0.80 (3H, t), 0.60 (2H, m), 0.40 (2H, m).

EXAMPLE 15

[1S-(1α,2β,3β,4α)]-4-[7-(Cyclopropylamino)-5-(propylthio)-3H-1,2,3-triazolo[4,5-d]pyrimidin-3-yl]-N-ethyl-2,3-dihydroxy-cyclopentanecarboxamide The title compound was prepared according to the method of Example 7, step e) using cyclopropanamine.

Mpt 192° C.

MS (APCI) 422 (M+H$^+$, 100%).

NMR δH (d$_6$-DMSO) 9.07 (1H, d), 7.92 (1H, s), 5.12 (1H, d), 4.98–4.92 (2H, m), 4.44–4.39 (1H, m), 4.10–4.09 (1H, m), 3.42–3.04 (6H, m), 2.76–2.67 (1H, m), 2.35–2.19 (2H, m), 1.75–1.67 (2H, m), 1.09–0.68 (9H, m).

EXAMPLE 16

[1S-[1α,2β,3β,4α(1S*,2R*)]]-N-Ethyl-2,3-dihydroxy-4-[7-[(2-phenylcyclopropyl)amino]-5-[[3-(trifluoromethyl)phenyl]thio]-3H-1,2,3-triazolo[4,5-d]pyrimidin-3-yl]-cyclopentanecarboxamide The title compound was prepared according to the method of Example 4, step b) using 3-(trifluoromethyl)thiophenol.

MS (APCI) 600 (M+H⁺, 100%).

NMR δH (d₆-DMSO) (363K) 9.09 (1H, d), 7.90 (2H, m), 7.70 (1H, d), 7.56 (2H, s), 7.26 (2H, t), 7.17 (1H, d), 7.08 (2H, s), 4.85 (1H, dd), 4.78 (1H, dd), 4.61 (1H, d), 4.40 (1H, dd), 4.10 (1H, dd), 3.10 (2H, m), 3.01 (1H, m), 2.70 (1H, m), 2.32–2.20 (2H, m), 2.13 (1H, dd), 1.38 (1H, m), 1.06 (1H, m), 1.02 (3H, t).

EXAMPLE 17 a) [1S-[1α,2β,3β,4α(1S*,2R*)]]-N-Ethyl-2,3-dihydroxy-4-[7-[(3-phenylpropyl)amino]-5-(propylthio)-3H-1,2,3-triazolo[4,5-d]pyrimidin-3-yl]-cyclopentanecarboxamide The title compound was prepared according to the method of Example 7, step e) using 3-phenylpropylamine.

Mpt 206–207° C.

MS (APCI) 500 (M+H⁺, 100%).

NMR δH (d₆-DMSO) 9.04 (1H, t), 7.92 (1H, t), 7.30–7.13 (5H, m), 5.11 (1H, d), 4.93 (1H, dd), 3.55 (2H, dd), 3.18–3.01 (4H, m), 2.78–2.62 (3H, m), 2.40–2.20 (2H, m), 2.00–1.86 (2H, m), 1.78–1.62 (2H, m), 1.02 (3H, t), 0.98 (3H, t).

EXAMPLE 18

[1S-[1α,2β,3β,4α(1S*,2R*)]]-2,3-Dihydroxy-N-methyl-4-[7-[(2-phenylcyclopropyl)amino]-5-(propylthio)-3H-1,2,3-triazolo[4,5-d]pyrimidin-3-yl]-cyclopentanecarboxamide a) [3aR-[3aα,4α,6α(1R*,2S*),6aα]]-Tetrahydro-2,2-dimethyl-N-methyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxamide The subtitle compound was prepared according to the method of Example 1, step d) using methylamine hydrochloride.

MS (APCI) 524 (M+H⁺, 100%).

b) [1S-[1α,2β,3β,4α(1S*,2R*)]]-2,3-Dihydroxy-N-methyl-4-[7-[(2-phenylcyclopropyl)amino]-5-(propylthio)-3H-1,2,3-triazolo[4,5-d]pyrimidin-3-yl]-cyclopentanecarboxamide A solution of the product from step (a) (0.26 g) in trifluoroacetic acid (16 ml)/water (4 ml) was stirred at room temperature for 2 hours. The reaction mixture was concentrated and purified (SiO₂, 96:4 dichloromethane:methanol as eluant) to afford the title compound (0.16 g).

Mp 165–166° C.

MS (APCI) 484 (M+H⁺, 100%).

NMR δH (d₆-DMSO) 9.35 (1H, d, J=4.2 Hz), 7.88 (1H, q, J=4.5 Hz), 7.29–7.18 (5H, m), 5.13 (1H, d, J=5.7 Hz), 5.00–4.91 (2H, m), 4.41 (1H, q, J=7.2 Hz), 4.11 (1H, q, J=4.8 Hz), 3.24–3.17 (1H, m), 3.01–2.80 (2H, m), 2.78–2.70 (1H, m), 2.60 (3H, d, J=4.5 Hz), 2.37–2.20 (2H, m), 2.18–2.09 (1H, m), 1.57–1.42 (3H, m), 1.38–1.27 (1H, m), 0.81 (3H, t, J=7.2 Hz).

EXAMPLE 19 a) [1S-[1α,2β,3β,4α)]]-N-Ethyl-2,3-dihydroxy -b 4-[7-[(4-phenylbutyl)]amino]-5-propylthio-1,2,3-triazolo[4,5-d]pyrimidin-3-yl]-cyclopentanecarboxamide The title compound was prepared according to the method of Example 7, step e) using 4-phenylbutylamine and ethanol in place of NN-dimethylformamide and methanol in the place of ethyl acetate.

Mpt 194–195° C.

MS (APCI) 514 (M+H⁺, 100%).

NMR δH (d₆-DMSO) 8.90 (1H, t), 7.91 (1H, t), 7.30–7.10 (5H, m), 5.12 (1H, d), 4.95 (1H, d), 4.92 (1H, d), 4.42 (1H, m), 4.10 (1H, m), 3.53 (2H, m), 3.20–3.00 (4H, m), 2.80–2.70 (1H, m), 2.60 (2H, t), 2.40–2.20 (2H, m), 1.75–1.60 (6H, m), 1.00 (6H, m)

EXAMPLE 20

[1S-[1α,2β,3β,4α(1S*,2R*)]]-2,3-Dihydroxy-4-[5-(methylthio)-7-[(2-phenylcyclopropyl)amino]-3H-1,2,3-triazolo[4,5-d]pyrimidin-3-yl]-N-phenyl cyclopentanecarboxamide a) [3aR-[3aα,4α,6α(1R*,2S*),6aα]]-Tetrahydro-2,2-dimethyl-6-[7-[(2-phenylcyclopropyl)amino]-5-(propylsulphonyl)-3H-1,2,3-triazolo[4,5-d]pyrimidin-3-yl]-4H-cyclopenta-1,3-dioxole-4-carboxylic acid Prepared according to the method of Example 4, step a) using the product of Example 1, step c).

MS (APCI) 543 (M+H⁺, 100%).

b) [3aR-[3aα,4α,6α(1R*,2S*)6aα]]-Tetrahydro-2,2-dimethyl-6-[5-(methylthio)-7-(2-phenylcyclopropyl)amino-3H-1,2,3-triazolo[4,5-d]pyrimidin-3-yl]-4H-cyclopenta-1,3-dioxole-4-carboxylic acid Sodium thiomethoxide (0.52 g) was added to the product of step a) in tetrahydrofuran (10 ml). The reaction was stirred for 2 hours then added slowly to a saturated aqueous solution of sodium chloride (20 ml) before extraction with ethyl acetate (2×50 ml). The organic phase was dried and concentrated to afford the subtitle compound.

MS (APCI) 483 (M+H⁺, 100%).

c) [1S-[1α,2β,3β,4α(1S*,2R*)]]-2,3-Dihydroxy-4-[5-(methylthio)-7-[(2-phenylcyclopropyl)amino]-3H-1,2,3-triazolo[4,5-d]pyrimidin-3-yl]-N-phenyl cyclopentanecarboxamide The title compound was prepared according to the method of example 1, step d) using the product of step b) and aniline, followed by deprotection according to the method of example 1, step e).

MS (APCI) 518 (M+H⁺, 100%).

NMR δH (d₆-DMSO) 10.10 (1H, s), 9.40 (1H, d), 7.65 (2H, d), 7.40–7.20 (7H, m), 7.04 (1H, t), 5.25 (1H, d), 5.20 (1H, d), 5.05 (1H, dd), 4.42 (1H, dd), 4.30 (1H, dd), 3.20 (1H, m), 3.05 (1H, m), 2.35 (3H, s), 2.12 (1H, m), 1.43 (1H, m), 1.37 (1H, m).

EXAMPLE 21

[1-[1α,2β,3β,4α(1S*,2R*)]]-4-[5-[4-[(Acetylamino)phenyl]thio]-7-[(2-phenylcydopropyl)amino]-3H-1,2,3-triazolo[4,5-d]pyrimidin-3-yl]-N-ethyl-2,3-dihydroxy-cyclopentanecarboxamide The title compound was prepared according to the method of example 4, step b) using 4-(acetylamino)thiophenol.

MS (APCI) 589 (M+H⁺, 100%).

NMR δH (d₆-DMSO) 9.31 (1H, d), 7.92 (1H, m), 7.63 (2H, d), 7.52 (2H, d), 7.27 (2H, t), 7.17 (1H, t), 7.00 (2H, d), 4.85 (1H, dd), 4.37 (1H, dd), 4.07 (1H, dd), 3.09 (2H, m), 2.70 (1H, m), 2.40–2.19 (3H, m), 2.09 (3H, s), 1.30 (1H, m), 1.05 (4H, m).

EXAMPLE 22

[1S-[1α,2β,3β,4α(1S*,2R*)]]-4-[5-[(3-Chlorophenyl)thio]-7-[(2-phenylcyclopropyl)amino]-3H-1,2,3-triazolo[4,5-d]pyrimdin-3-yl]-N-ethyl-2,3-dihydroxy-cyclopentanecarboxamide The title compound was prepared according to the method of example 4, step b) using 3-chlorothiophenol.

MS (APCI) 566 (M+H⁺, 100%).

NMR δH (d₆-DMSO) 9.40 (1H, d), 7.92 (1H, t), 7.70 (1H, s), 7.55 (1H, d), 7.55 (1H, d), 7.43 (1H, d), 7.35 (1H, t), 7.31 (2H, t), 7.18 (1H, t), 7.04 (2H, d), 5.11 (1H, d), 5.06 (1H, d), 4.95 (1H, dd), 4.38 (1H, dd), 4.07 (1H, dd), 3.10 (3H, m), 2.72 (1H, m), 2.40–1.90 (3H, m), 1.38 (1H, m), 1.12 (1H, dd), 1.03 (3H, t).

EXAMPLE 23

[1S-[1α,2β,3β,4α(1S*,2R*)]]-4-[5-[(4-Chlorophenyl)thio]-7-[(2-phenylcyclopropyl)amino]-3H-1,2,3-triazolo[4,5-d]pyrimidin-3-yl]-N-ethyl-2,3-dihydroxy-cyclopentanecarboxamide The title compound was prepared according to the method of example 4, step b) using 4-chlorothiophenol.

MS (APCI) 566 (M+H⁺, 100%).

NMR δH (d₆-DMSO) 9.40 (1H, d), 7.92 (1H, t), 7.65 (2H, d), 7.30 (4H, m), 7.20 (1H, m), 7.06 (2H, d), 5.12 (1H, d), 4.98 (1H, d), 4.90 (1H, m), 4.36 (1H, dd), 4.05 (1H, m), 3.10 (3H, m), 2.40–2.10 (3H, m), 1.41 (1H, m), 1.14 (1H, m), 1.04 (3H, t).

EXAMPLE 24

[1S-[1α,2β,3β,4α(1S*,2R*)]]-4-[5-[4-(1,1-Diethylethyl)-phenyltio]-7-[(2-phenylcyclopropyl)amino]-3H-1,2,3-triazolo[4,5-d]pyrimidin-3-yl]N-N-ethyl-2,3-dihydroxy-cyclopentanecarboxamide The title compound was prepared according to the method of example 4, step b) using 4-(1,1-dimethylethyl)thiophenol.

MS (APCI) 588 (M+H⁺, 100%).

NMR δH (d₆-DMSO) 9.40 (1H, d), 7.92 (1H, t), 7.50 (2H, d), 7.35 (2H, d), 7.29 (2H, t), 7.20 (1H, m), 7.09 (2H, d), 5.11 (1H, d), 4.91 (1H, d), 4.87 (1H, dd), 4.37 (1H, dd), 4.03 (1H, dd), 3.10 (3H, m), 2.71 (1H, m), 2.40–2.10 (3H, m), 1.33 (1H, m), 1.26 (9H, s), 1.07 (1H, m), 1.03 (3H, t).

EXAMPLE 25

[1S-[1α,2β,3β,4α(1S*,2R*)]]-N-Ethyl-2,3-dihydroxy-4-4-[7-[(2-phenylcyclopropyl)amino]-5-(phenylthio)-3H-1,2,3-triazolo[4,5-d]pyrimidin-3-yl]-cyclopentanecarboxamide The title compound was prepared according to the method of example 4, step b) using thiophenol.

MS (APCI) 532 (M+H⁺, 100%).

NMR δH (d₆-DMSO) 9.30 (1H, d), 7.90 (1H, t), 7.58 (2H, d), 7.45–7.25 (6H, m), 7.17 (2H, t), 7.05 (2H, d), 5.09 (1H, d), 4.95 (1H, d), 4.86 (1H, dd), 4.36 (1H, dd), 4.05 (1H, dd), 3.10 (3H, m), 2.71 (1H, m), 2.30–2.10 (3H, m), 1.37 (1H, m), 1.13 (1H, dd), 1.03 (3H, t).

EXAMPLE 26

[1S-[1α,2β,3β,4α(1S*,2R*)]]-4-[5-[(2-Chlorophenyl)thio]-7-[(2-phenylcyclopropyl)amino]-3H-1,2,3-triazolo[4,5d]pyrimidin-3-yl]-N-ethyl-2,3-dihydroxy-cyclopentanecarboxamide The title compound was prepared according to the method of example 4, step b) using 2-chlorothiophenol.

MS (APCI) 566 (M+H⁺, 100%).

NMR δH (d₆-DMSO) 9.02 (1H, d), 7.60 (1H, d), 7.54 (1H, d), 7.48 (1H, m), 7.40 (1H, t), 7.26 (3H, m), 7.15 (1H, t), 7.07 (2H, bs), 4.85 (1H, d), 4.77 (1H, d), 4.38 (1H, dd), 4.07 (1H, dd), 3.11 (3H, m), 2.70 (1H, m), 2.30 (2H, m), 2.18 (1H, m), 1.36 (1H, m), 1.10 (1H, m), 1.03 (3H, t).

EXAMPLE 27

[1S-(1α,2β,3β,4α)]-4-[7-(Butylamino)-5-(propylthio)-3H-1,2,3-triazolo[4,5d]pyrimidin-3-yl]-N-ethyl-2,3-dihydroxy-cyclopentanecarboxamide The title compound was prepared according to the method of example 7, step e) using the product of example 7, step d) and butylamine.

MS (APCI) 438 (M+H⁺, 100%).

NMR δH (d₆-DMSO)) 8.99 (1H, t), 7.92 (1H, t), 5.11 (1H, d), 4.95 (2H, m), 4.43 (1H, m), 3.48 (2H, dd), 3.10 (4H, m), 2.73 (1H, ddd), 2.40–2.18 (2H, m), 1.80–1.52 (4H, m) 1.42–132 (2H, m), 1.03 (3H, t), 1.01 (3H, t), 0.90 (3H, t).

EXAMPLE 28

[1S-[1α,2β,3β,4α(1S*,2R*)]]-N-Ethyl-2,3-dihydroxy-4-[5-[4-(1-methylethyl)-phenylthio]-7-[(2-phenylcyclopropyl)amino]-3H-1,2,3-txiazolo[4,5-d]pyrimidin-3-yl]-cyclopentanecarboxamide The title compound was prepared according to the method of example 4, step b) using 4-(1-methylethyl)thiophenol.

MS (APCI) 574 (M+H⁺, 100%).

NMR δH (d₆-DMSO) 9.32 (1H, d), 7.91 (1H, t), 7.49 (2H, d), 7.27 (2H, d), 7.20 (3H, m), 7.10 (2H, d), 5.11 (1H, d), 4.91 (1H, d), 4.37 (1H, d), 4.05 (1H, d), 3.11 (3H, m), 2.91 (1H, m), 2.71 (1H, m), 2.40–2.10 (3H, m), 1.30 (1H, m), 1.18 (6H, d), 1.17 (1H, m), 1.03 (3H, t).

EXAMPLE 29

[1S-[1α,2δ,3δ,4α(1S*,2R*)]]-N-Ethyl-2,3dihydroxy-4-[5-(naphth-2ylthio)-7-[(2 heykycloropropyl)amino]-3H-1,2,3-triazolo[4,5d]pyrimidin-3-yl]-cyclopentanecarboxamide The title compound was prepared according to the method of example 4, step b) using 2-naphthylthiol.

MS (APCI) 574 (M+H⁺, 100%).

NMR δH (d₆-DMSO) 9.31 (1H, d), 8.22 (1H, s), 7.90 (3H, m), 7.81 (1H, d), 7.68 (1H, d), 7.59 (2H, t), 7.10 (3H, m), 6.76 (2H, m), 5.13 (1H, d), 4.98 (1H, d), 4.91 (1H, dd), 4.37 (1H, dd), 4.05 (1H, m), 3.10 (2H, m), 3.08 (1H, m), 2.72 (1H, m), 2.30–2.10 (3H, m), 1.25 (1H, m), 1.03 (3H, t), 0.86 (1H, dd).

EXAMPLE 30

[1S-[1α,2β3β,4α(1S*,2R*)]]-N-Cyclopropyl-2,3dihydroxy-4-[5-(methylthio)-7-[(2-phenylcyclopropyl)amino]-3H-1,2,3triazolo[4,5d]pyrimidin3-yl]cyclopentanecarboxamide The title compound was prepared according to the method of example 1, step d) using the product of Example 20, step b) and cyclopropylamine, followed by deprotection according to the method of example 1, step e).

MS (APCI) 482 (M+H⁺, 100%).

NMR δH (d₆-DMSO) 9.36 (1H, d), 8.00 (1H, d), 7.20 (5H, m), 5.15 (1H, d), 4.95 (2H, m), 4.43 (1H, dd), 4.17 (1H, dd), 3.20 (1H, m), 2.70 (2H, m), 2.35 (3H, s), 2.25 (2H, m), 2.17 (1H, m), 1.46 (1H, m), 1.38 (1H, dd), 0.60 (2H, d), 0.40 (2H, s).

EXAMPLE 31

[1S-(1α,2β,3β,4α)]-N-Ethyl-2,3-dihydroxy-4-[7-[(2-phenylethyl)amino]-5-(propylthio)-3H-1,2,3-triazolo[4,5d]pyrimidin-3yl]-cyclopentanecarboxamide The title compound was prepared according to the method of Example 7, step e), using (2-phenyl)ethylamine in ethanol.

Mpt 215–7° C.

MS (APCI) 486 (M+H$^+$, 100%).

NMR δH (d$_6$-DMSO) 8.72 (1H, t), 7.91 (1H, t), 7.30–7.10 (5H, m), 5.12 (1H, d), 4.95 (1H, d), 4.95 (1H, m), 4.41 (1H, m), 4.11 (1H, m), 3.72 (2H, m), 3.12–2.93 (6H, m), 2.82 (2H, m), 2.73 (1H, m), 1.70 (2H, m), 0.98 (6H, m).

EXAMPLE 32

[1S-[1α,2β,3β,4α(1S*,2R*)]]-2,3-Dihydroxy-[4-[7-[(2-phenylcyclopropyl)amino]-5-(propylthio)-3H-1,2,3-triazolo[4,5d]pyrimidin-3-yl]-N-prop-2-ynyl-cyclopentanecarboxamide The title compound was prepared according to the method of example 1, step d) using the product of example 1, step c) and propargylamine, followed by deprotection according to the method of example 18, step b).

Mpt 176–177° C.

MS (APCI) 508 (M+H$^+$, 100%).

NMR δH (d$_6$-DMSO) 9.36 (1H, d), 8.41 (1H, t), 7.35–7.16 (5H, m), 5.15 (1H, d), 5.04–4.93 (2H, m), 4.43 (1H, q), 4.11 (1H, q), 3.88 (2H, s), 3.22–3.18 (1H, m), 3.11 (1H, s), 2.99–2.93 (1H, m), 2.90–2.76 (2H, m), 2.40–2.10 (3H, m), 1.55–1.43 (3H, m), 1.35 (1H, q), 0.81 (3H, t).

EXAMPLE 33

[1S-[1α,2β,3β,4α(1S*,2R*)]]-2,3-Dihydroxy-4-[7-[(2-phenylcyclopropyl)amino]5-(propylthio)-3H-1,2,3-triazolo[4,5d]pyrimidin-3-yl]-N-(2,2,2-trifluoroethyl)-cyclopentanecarboxamide The title compound was prepared according to the method of example 1, step d) using the product of example 1, step c) and 2,2,2-trifluoroethylamine hydrochloride, followed by deprotection according to the method of example 18, step b).

Mpt 195–196° C.

MS (APCI) 552 (M+H$^+$, 100%).

NMR δH (d$_6$-DMSO) 9.36 (1H, d), 8.64 (1H, t), 7.31–7.16 (5H, m), 5.15 (1H, br s), 5.00 (1H, q), 4.45–4.41 (1H, m), 4.13 (1H, t), 3.97–3.90 (2H, m), 3.22–3.18 (1H, m), 3.00–2.80 (3H, m), 2.42–2.35 (1H, m), 2.30–2.19 (1H, m), 2.18–2.10 (1H, m), 1.55–1.45 (3H, m), 1.36–1.31 (1H, m), 0.81 (3H, t).

EXAMPLE 34

[1S-[1α,2β,3β,4α(1S*,2R*)]]-N-Ethyl-4-[[2-(4-fluorophenyl) cyclopropyl]amino]-5(propylthio)-3H-1,2,3-triazolo[4,5d]pyrimidin-3-yl]-2,3dihydroxy-cyclopentanecarboxamide a) (3aS-[1(E),3aα,6α,7aβ]]-1-[3-(4-Fluorophenyl)-1-oxo-2-propenyl]-hexahydro-8,8-dimethyl-3H-3a,6-methano-2,1-benzisothiazole-2,2-dioxide A mixture of 3-(4-fluorophenyl)-2-propenoic acid (3.0 g) and thionyl chloride (5 ml) was stirred at 70° C. for 1 hour, the reaction mixture was then concentrated under reduced pressure. The residue was azeotroped twice with dichloromethane then dissolved in toluene (10 ml). To a suspension of sodium hydride (60% dispersion in oil; 0.99 g) in toluene (40 ml) was added a solution of [3aS-(3aα,6α,7aβ)]-hexahydro-8,8-dimethyl-3H-3a,6-methano-2,1-benzisothiazole-2,2-dioxide (3.89 g) in toluene (40 ml) and the mixture stirred for 30 minutes. To the reaction mixture was then added the solution described above and the resulting suspension was stirred for 16 hours. Water (200 ml) was added, the organics collected and the aqueous extracted into dichloromethane (3×100 ml). The organics were combined, dried and concentrated. Recrystallisation (ethanol) gave the subtitle compound as colourless needles (5.92 g).

MS (APCI) 364 (M+H$^+$, 100%)

b) [3aS-[1(1S*,2S*),3aα,6α,7aβ]]-1-[[2-(4Fluorophenyl) cyclopropyl]carbonyl]-hexahydro-8,8dimethyl-3H-3a,6-methano-2,1-benzisothiazole-2,2-dioxide A solution of diazomethane (2.9 g) in ether (150 ml) (prepared as described in Vogel's Textbook of Practical Organic Chemistry, Fifth Edition, Longman scientific and technical, p432) was added to a solution of the product of step a) (5.90 g) and palladium(II) acetate (18 mg) in dichloromethane (350 ml) at 0° C. and the reaction mixture stirred at 0° C. for 5 hours. Acetic acid (5 ml) was added and the reaction mixture was then washed with saturated sodium bicarbonate solution (200 ml) and the organics filtered through a plug of silica. After concentrating in vacuo, the residue was recrystallised (ethanol) to give the subtitle compound as colourless needles (3.81 g).

MS (APCI) 378 (M+H$^+$, 100%)

c) (1R-trans)-2-(4-Fluorophenyl)-cyclopropanecarboxylic acid

A suspension of the product from step b) (3.74 g) and lithium hydroxide monohydrate (4.1 g) in tetrahydrofuran (100 ml)/water (3 ml) was stirred at 50° C. for 24 hours. The reaction mixture was concentrated in vacuo, and the residue dissolved in water (100 ml), acidified with 2M HCl and extracted into dichloromethane (3×75 ml). The organics were dried and concentrated. Purification (SiO$_2$, isohexane:diethylether 2:1 as eluant) gave the subtitle compound as a colourless solid (1.78g).

MS (APCI) 179 (M–H$^+$, 100%)

d) (1R-trans)-2-(4-Fluorophenyl)cyclopropanamine

To a solution of the product from step c) (2.6 g) and triethylamine (2.7 ml) in acetone/water (10:1, 33 ml) at 0° C. was added ethyl chloroformate (2.0 ml) over 5 min. The solution was maintained at 0° C. for 30 minutes before addition of sodium azide (1.52 g) in water (6 ml). After a further hour, water (350 ml) was added and the reaction mixture extracted with toluene (3×100 ml). The organic extracts were combined and dried, then heated at reflux for 2 hours behind a blast screen. After cooling the solution, 6M HCl (50 ml) was added and the mixture heated at reflux for 3 hours. Water (150 ml) was added and the aqueous phase basified with 2M NaOH (aq), then extracted into dichloromethane (3×100 ml). The organic phase was dried and concentrated to give the subtitle compound as a colourless oil (1.31 g).

NMR δH (CDCl$_3$) 0.88–0.95 (1H, m), 0.99–1.06 (1H, m), 1.81–1.87 (1H, m), 2.47–2.52 (1H, m), 6.90–7.00 (4H, m)

e) [1S-[1α,2β,3β,4α(1S*,2R*)]]-N-Ethyl-4-[7-[[2-(4-fluorophenyl) cyclopropyl]amino]-5-(propylthio)-3H-1,2,3-triazolo[4,5d]pyrimidin-3-yl]-2,3-dihydroxy-cyclopentanecarboxamide The title compound was prepared according to the method of Example 7, step (e) using the products of step (d) and Example 7, step (d).

MS (APCI) 516 (M+H$^+$, 100%)

NMR δH (d$_6$-DMSO) 9.35 (1H, d), 7.95–7.92 (1H, m), 7.27–7.09 (4H, m), 5.16–5.10 (1H, m), 5.01–4.93 (2H, m), 4.48–4.40 (1H, m), 4.14–4.08 (1H, m), 3.19–3.06 (3H, m), 3.02–2.82 (2H, m), 2.78–2.70 (1H, m), 2.37–2.10 (3H, m), 1.57–1.28 (4H, m), 1.03 (3H, t), 0.82 (3H, t).

EXAMPLE 35

[1S-[1α,2β,3β,4α(1S*,2R*)]]-[4-[7-[[2-(4-Chlorophenyl) cyclopropyl]amino]-5-(propylthio)-3H-1,2,3-triazolo[4,5-d]pyrimidin-3-yl]-N-ethyl-2,3-dihydroxy-cyclopentanecarboxamide a) (1R-trans)-2-(4-Chlorophenyl)cyclopropanecarboxylic acid The subtitle compound was prepared according to the method of Example 7, step (a) using 3-chloro-1-ethenylbenzene.

b) (1R-trans)-2-(4-Chlorophenyl)cyclopropanamine, [R-(R*,R*)]-2,3-dihydroxybutanedioate (1:1)

The subtitle compound was prepared according to the method of Example 7, step (b) using the product from step (a).

NMR δH (d$_6$-DMSO) 7.32 (2H, d), 7.14 (2H, d), 3.95 (2H, d), 2.71–2.65 (1H, m), 1.99–1.88 (1H, m), 1.30–1.20 (1H, m), 1.11 (1H, q)

mpt 161–2° C.

c) [1S-[1α,2β,3β,4α(1S*,2R*)]]-[4-[7-[[2-(4-Chlorophenyl)cyclopropyl]amino]-5-(propylthio)-3H-1,2,3-triazolo[4,5-d]pyrimidin-3-yl]-N-ethyl-2,3-dihydroxy-cyclopentanecarboxamide The subtitle compound was prepared according to the method of Example 7, step (e) using the products from step (b) and Example 7, step (d).

NMR δH (d$_6$-DMSO) 9.38–9.37 (1H, m), 7.94–7.90 (1H, m), 7.33–7.32 (2H, m), 7.24–7.18 (2H, m), 5.13–5.11 (1H, m), 4.98–4.94 (2H, m), 4.44–4.41 (1H, m), 4.13–4.08 (1H, m), 3.06–3.04 (2H, m), 2.96–2.80 (2H, m), 2.71–2.67 (1H, m), 2.34–2.12 (2H, m), 2.22–2.10 (1H, m), 1.58–1.44 (3H, m), 1.37–1.32 (1H, m), 1.04–0.97 (3H, t), 0.81 (3H, t)

MS (APCI) 532 (M+H$^+$, 100%)

EXAMPLE 36

[1S-[1α,2β,3β,4α(1S*,2R*)]]-N-Cyclopentyl-2,3-dihydroxy-4-[5-(methylthio)-7-[(2-phenylcyclopropyl)amino]-3H-1,2,3-triazolo[4,5-d]pyrimidin-3-yl]-cyclopentanecarboxamide The title compound was prepared according to the method of example 1, step d) using the product of Example 20, step b) and cyclopentylamine, followed by deprotection according to the method of example 1, step e).

MS (APCI) 510 (M+H$^+$, 100%).

NMR δH (d$_6$-DMSO) 9.35 (1H, d), 7.90 (1H, d), 7.20 (5H, m), 5.20 (1H, d), 4.95 (2H, m), 4.53 (1H, dd), 4.10 (1H, dd), 4.00 (1H, dd), 3.20 (1H, m), 2.78 (1H, m), 2.35 (3H, s), 2.25 (3H, m), 1.80 (2H, m), 1.60–1.30 (8H, m).

EXAMPLE 37

[1S-[1α,2β,3β, 4α(1S*,2R*)]]-2,3-Dihydroxy-N-(1,1-dimethylethyl)-4-[7-[(2-phenylcyclopropyl)amino]-5-(propylthio)-3H-1,2,3-triazolo[4,5-d]pyrmidin-3-yl]-cyclopentanecarboxamide The title compound was prepared according to the method of example 1, step d), using 1,1-dimethylethylamine, followed by deprotection according to the method of example 1, step e).

Mpt 110–112° C.

MS (APCI) 526 (M+H$^+$, 100%).

NMR δH (d$_6$-DMSO) 9.35 (1H, d), 7.50 (1H, s), 7.31–7.16 (5H, m), 5.11 (1H, d), 4.98–4.91 (2H, m), 4.45–4.40 (1H, m), 4.07–4.04 (1H, m), 3.24–3.18 (1H, m), 3.00–2.81 (2H, m), 2.79–2.73 (1H, m), 2.33–2.18 (2H, m), 2.15–2.10 (1H, m), 1.54–1.44 (3H, m), 1.35–1.22 (1H, m), 1.26 (9H, s), 0.80 (3H, t).

EXAMPLE 38

[1S-(1α,2β,3β,4α)]-N-Ethyl-2,3dihydroxy-[4-[7-[(2-phenylamino)ethylamino]-5-(propylthio)-3H-1,2,3-triazolo[4,5-d]pyrimidin-3-yl]-cyclopentanecarboxamide The title compound was prepared according to the method of example 7, step e) using the product of example 7, step d) and (N-phenyl)ethylenediamine.

Mpt 186–187° C.

MS (APCI) 501 (M+H$^+$, 100%).

NMR δH (d$_6$-DMSO) 9.00 (1H, t), 7.92 (1H, t), 7.08 (2H, t), 6.65 (2H, d), 6.53 (3H, t), 5.75 (1H, br s), 5.15 (1H, br s), 5.05–4.92 (2H, m), 4.45 (1H, t), 4.11 (1H, t) 3.65 (2H, q), 3.29 (1H, br s), 3.14–3.05 (4H, m), 2.78–2.70 (1H, m), 2.37–2.19 (2H, m), 1.77–1.65 (2H, m), 1.05–0.95 (5H, m).

EXAMPLE 39

[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-N-(phenylmethyl)-cyclopentanecarboxamide a) [3aR-[3aα,4α,6α(1R*,2S*),6aα]]-Tetrahydro-2,2-dimethyl-6-[7-[(2-phenylcyclopropyl)amino]-5-(propylthio)-3H-1,2,3-triazolo[4,5-d]pyrimidin-3-yl]-N-(phenylmethyl)-4H-cyclopenta-1,3-dioxole-4carboxamide N,N-Diisopropylethylamine (3 eq) was added to a solution of 2-(1H-benzotriazole-1-yl)-1,1,3,3-tetramethyluronium tetrafluoroborate (1.5 eq), 1-hydroxybenzotriazole hydrate (1.5 eq), benzylamine (2 eq) and the product of Example 1, step c) (1 eq) in DMF (20 ml). The reaction mixture was stirred at room temperature for 2 hours then added dropwise to stirred acidic ice-water. The subtitle compound was isolated by filtration.

MS (APCI) 600 (M+H$^+$, 100%).

b) [1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-N-(phenylmethyl)-cyclopentanecarboxamide A solution of the product from step a) in methanol (20 ml)/2M aqueous hydrochloric acid (5 ml) was stirred at room temperature for 2 hours. The resulting solid was collected by filtration then recrystallised (methanol/water) to afford the title compound.

Mpt 195–197° C.

MS (APCI) 560 (M+H$^+$, 100%).

NMR δH (d$_6$-DMSO) 9.35 (1H, d), 8.46–8.44 (1H, t), 7.34–7.15 (5H, m), 5.16–4.94 (3H, m), 4.48–4.42 (1H, m), 4.32–4.29 (2H, m), 4.19–4.14 (1H, m), 3.21 (1H, m), 2.98–2.81 (3H, m), 2.40–2.13 (4H, m), 1.54–1.31(3H, m), 0.77 (3H, t).

EXAMPLE 40

[1S-[1α,2β,3β,4α(1S*,2R*)]]-N-(2-Fluoroethyl)-2,3-dihydroxy-4-7-[(2-phenylcyclopropyl)amino]-5-(propylthio)-3H-1,2,3-triazolo[4,5-d]pyrimidin-3-yl]-cyclopentanecarboxamide The title compound was prepared according to the method of example 39, step a) using the product from example 1, step c) and 2-fluoroethylamine hydrochloride, followed by deprotection according to the method of example 39, step b)

Mpt 168–9° C.

MS (APCI) 516 (M+H+, 100%).

NMR δH (d$_6$-DMSO) 9.34 (1H, d), 8.21 (1H, t), 7.31–7.15 (5H, m), 5.14 (1H, d), 5.01–4.95 (2H, m), 4.51 (1H, t), 4.35 (1H, t), 4.42 (1H, q), 4.11 (1H, d), 3.50–3.40 (1H, m), 3.40–3.30 (1H, m), 3.25–3.15 (1H, m), 2.94–2.72 (3H, m), 2.37–2.15 (3H, m), 1.58–1.43 (2H, m), 1.38–1.31 (1H, m), 0.81 (3H, t).

EXAMPLE 41

[1S-[1α,2β,3β,4α(1S*,2R* )]]-1-[2,3-Dihydroxy-4-[7-[(2-phenylcyclopropyl)amino]-5-(propylthio)-3H-1,2,3-triazolo[4,5-d]pyrimidin -3-yl]-cyclopentylcarbonyl]-4-methyl-piperidine The title compound was prepared according to the method of example 39, step a) using the product from example 1, step c) and 4-methyl-piperidine, followed by deprotection according to the method of example 39, step b).

Mpt 209° C.

MS (APCI) 552 (M+H+, 100%).

NMR δH (d$_6$-DMSO) 9.34 (1H, d), 7.31–7.15 (5H, m), 5.15–5.01 (4H, m), 4.45–3.95 (4H, m), 3.20–2.72 (7H, m), 2.37–2.13 (5H, m), 1.62–1.31 (5H, m), 0.93–0.78 (6H, m).

EXAMPLE 42

[1S-(1α,2β,3β,4α)]-4-[7-[2-[(2-Chlorophenyl)ethyl]amino]-5-(propylthio)-3H-1,2,3-triazolo[4,5-d]pyrimidin-3-yl]-N-ethyl-2,3-dihydroxy-cyclopentanecarboxamide The title compound was prepared according to the method of Example 7, step e) using 2-(2-chlorophenyl)ethylamine.

Mpt 200–2° C.

MS (APCI) 520/2 (M+H+, 100%).

NMR δH (d$_6$-DMSO) 8.75 (1H, t), 7.91 (1H, t), 7.20–7.45 (4H, m), 5.12 (1H, d), 4.98 (1H, d), 4.93 (1H, m), 4.35 (1H, m), 4.13 (1H, m), 3.77 (2H, m), 3.10 (6H, m), 2.72 (1H, m), 2.30 (2H, m), 1.70 (2H, m), 0.99 (6H, m).

EXAMPLE 43

[1S-(1α,2β,3β,4α)]-N-Ethyl-2,3-dihydroxy-4-[7-[2-[(4-methoxyphenyl)ethyl]amino]-5-(propylthio)-3H-1,2,3-triazolo[4,5-d]pyrimidin-3-yl]-cyclopentanecarboxamide The title compound was prepared according to the method of Example 7, step e), using 2-(4-methoxyphenyl)ethylamine.

Mpt 236–7° C.

MS (APCI) 516 (M+H+, 100%).

NMR δH (d$_6$-DMSO) 8.65 (1H, t), 7.92 (1H, t), 7.18–6.86 (4H, ABq), 5.12 (1H, d), 4.96 (1H, d), 4.93 (1H, m), 4.43 (1H, m), 4.11 (1H, m), 4.10–3.70 (2H, m), 3.71 (3H, s), 3.10–2.87 (6H, m), 2.72 (1H, m), 2.31 (2H, m), 1.73 (2H, m), 1.01 (6H, m).

EXAMPLE 44

[1S-[1α,2β,3β,4α(1S*,2R*)]]-2,3-Dihydroxy-N-(2-hydroxyethyl)-N-methyl-4-[7-[(2-phenylcyclopropyl)amino]-5-(propylthio)-3H-1,2,3-triazolo[4,5-d]pyrimidin-3-yl]-cyclopentanecarboxamide The title compound was prepared according to the method of example 1, step d), using the product of example 1, step c) and 2-(methylamino)ethanol, followed by deprotection according to the method of example 1, step e).

Mpt 78–80° C.

MS (APCI) 528 (M+H+, 100%).

NMR δH (d$_6$-DMSO) 9.34 (1H, s), 7.29 (2H, t), 7.20–7.18 (3H, m), 5.13 (1H, d), 5.09–4.95 (2H, m), 4.82 (1H, t), 4.46 (1H, s), 4.11 (1H, s), 3.58–3.46 (2H, m), 3.38–3.30 (2H, m), 3.24–3.16 (1H, m), 3.09 (3H, s), 3.01–2.82 (3H, m), 2.40–2.26 (2H, m), 2.17–2.10 (1H, m), 1.56–1.45 (3H, m), 1.36–1.29 (1H, m),0.81 (3H, t).

EXAMPLE 45

[1S-[1α,2β,3β,4α(1S*,2R*)]]-2,3-Dihydroxy-N-(2-methoxyethyl)-4-[7-[(2-phenylcyclopropyl)amino]-5-(propylthio)-3H-1,2,3triazolo[4,5-d]pyrimidin-3-yl]-cyclopentanecarboxamide The title compound was prepared according to the method of example 1, step d), using the product of example 1, step c) and 2-methoxyethylamine, followed by deprotection according to the method of example 1, step e).

Mpt 173–174° C.

MS (APCI) 528 (M+H+, 100%).

NMR δH (d$_6$-DMSO) 9.35 (1H, s), 8.00 (1H, s), 7.29 (2H, t), 7.22–7.16 (3H, m), 5.13 (1H, s), 5.02–4.92 (2H, m), 4.44 (1H, s), 4.10 (1H, s), 3.40–3.29 (2H, m), 3.24 (6H, m), 3.01–2.72 (3H, m), 2.38–2.20 (2H, m), 2.17–2.10 (1H, m), 1.57–1.43 (3H, m), 1.36–1.26 (1H, m), 0.81 (3H, t).

EXAMPLE 46

[1S-(1α,2β,3β,4α)]-N-Ethyl-2,3-dihydroxy-[4-[7-[(2-phenoxyethyl)amino]-5-(propylthio)-3H-1,2,3-triazolo[4,5-d]pyrimidin-3-yl]-cyclopentanecarboxamide The title compound was prepared according to the method of example 7, step e) using the product of example 7, step d) and 2-phenoxyethylamine.

Mpt 195–196° C.

MS (APCI) 502 (M+H+, 100%).

NMR δH (d$_6$-DMSO) 9.15 (1H, t), 7.92 (1H, t), 7.27 (2H, t), 6.98–6.91 (3H, m), 5.12 (1H, d), 5.00–4.93 (2H, m), 4.45 (1H, q), 4.21 (2H, t), 4.11 (1H, q), 3.85 (2H, q), 3.13–3.03 (4H, m), 2.76–2.71 (1H, m), 2.37–2.19 (2H, m), 1.74–1.65 (2H, m), 1.06–0.95 (5H, m).

EXAMPLE 47

[1S-(1α,2β,3β,4α)]-4-[7-(Cyclopropylamino)-5-[(trifluoromethylphenyl)thio]-3H-1,2,3-triazolo[4,5-d]pyrimidin-3-yl]-N-ethyl-2,3-dihydroxy-cyclopentanecarboxamide The product of example 7, step d), cyclopropylamine (0.78 g) and N,N-diisopropylethylamine (1.75 g) in 1,4-dioxane (10 ml) was stirred at room temperature for 24 hours. The reaction mixture was concentrated and the residue dissolved in dichloromethane, m-chloroperoxybenzoic acid (1.0 g) added and the reaction mixture stirred for 30 minutes. The reaction mixture was washed twice with sodium metabisulphite solution, followed by saturated brine, then dried and concentrated. The residue was reacted without further purification according to the method of example 4, step b) using 4-trifluoromethylthiophenol, followed by deprotection according to the method of example 39, step b).

Mpt 209° C.

MS (APCI) 524 (M+H+, 100%).

NMR δH (d$_6$-DMSO) 9.24 (1H, d), 7.96–7.88 (3H, m), 7.82–7.79 (2H, d), 5.12–5.08 (1H, m), 4.96–4.86 (2H, m), 4.64–4.34 (1H, q), 4.05–4.00 (1H, q), 3.15–3.06 (2H, quint), 2.77–2.68 (2H, m), 2.37–2.12 (2H, m), 1.02 (3H, t), 0.89–0.57 (4H, m).

EXAMPLE 48

[1S-(1α,2β,3β,4α)]-4-[5-[(4-Chlorophenyl)thio]-7-(cyclopropylamino)-3H-1,2,3-triazolo[4,5-d]pyrimidin-3-yl]-N-ethyl-2,3-dihydroxy-cyclopentanecarboxamide The title compound was prepared according to the method of example 47 using 4-chlorothiophenol.

Mpt 221° C.

MS (APCI) 524 (M+H+, 100%).

NMR δH (d$_6$-DMSO) 9.18 (1H, d), 7.92–7.89 (1H, m), 7.71–7.63 (2H, m), 7.53–7.50 (2H, d), 5.11–5.09 (1H, d), 4.96–4.95 (1H, d), 4.86 (1H, t), 4.39–4.32 (1H, q), 4.06–4.03 (1H, m), 3.19–3.06 (2H, quint), 2.78–2.67 (2H, m), 2.30–2.12 (2H, m), 1.03 (3H, t), 0.88–0.60 (4H, m).

EXAMPLE 49

[1S-(1α,2β,3β,5α)]-4-[5-(Cyclohexylthio)-7-(cyclopropylamino)-3H-1,2,3-triazolo[4,5-d]pyrimidin-3-yl]-N-ethyl-2,3-dihydroxy-4-cyclopentanecarboxamide The title compound was prepared according to the method of example 47 using cyclohexanethiol.

Mpt 139° C.

MS (APCI) 462 (M+H+, 100%).

NMR δH (d$_6$-DMSO) 9.08 (1H, d), 7.91 (3H, t), 5.13–5.11 (1H, d), 4.95 (2H, q), 4.42 (1H, m), 4.13–4.09 (1H, m), 3.84 (1H, brs), 3.14–3.02 (3H, m), 2.74–2.69 (1H, m), 2.32–2.22 (2H, m), 2.09 (2H, brs), 1.71–1.20 (8H, m), 1.03 (3H, t), 0.78–0.67 (4H, m).

EXAMPLE 50

[1S-[1α,2β,3β,4α(1S*,2R*)]]N-[[3-(4-Fluorophenyl)propyl]amino]2,3-dihydroxy-4-[7-[(2-phenylcyclopropyl)amino]-5-(propylthio)-3H-1,2,3-triazolo[4,5-d]pyrimidin-3-yl]-cyclopentanecarboxamide a) [3aR-[3aα,4α,6α(1R*,2S*),6aα]]-N-[[3-(4-Fluorophenyl)propyl]amino]-6-[7-[(2-phenylcyclopropyl)amino]-5-(propylthio)-3H-1,2,3-triazolo[4,5-d]pyrimidin-3-yl]-tetrahydro-2,2-dimethyl-4H-cyclopenta-1,3-dioxole-4-carboxamide The product from example 7, step d), 3-(4-fluorophenyl)propyl)amine (Prepared as described by K Fujimura etal, Bioorganic Medicinal Chemistry, 1997, 5, 1675) and N,N-diisopropylethylamine in 1,4-dioxane (10 ml) was stirred at room temperature for 24 hours. The solvent was concentrated and the residue purified (SiO$_2$, ethyl acetate:isohexane, 1:1 as eluant) to afford the subtitle compound.

MS (APCI) 558 (M+H+, 100%).

b) [1S-[1α,2β,3β,4α(1S*,2R*)]]-N-Ethyl-2,3-dihydroxy-4-7-[(3-phenylpropyl)amino]-5-(propylthio)-3H-1,2,3-triazolo[4,5-d]pyrimidin -3-yl]cyclopentanecarboxamide The title compound was prepared according to the method of example 39, step b) using the product of step a).

Mpt 214–216° C.

MS (APCI) 518 (M+H+, 100%).

NMR δH (d$_6$-DMSO) 9.03 (1H, t), 7.91–7.90 (1H, t) 7.29–7.05 (4H, m), 5.12–4.93 (3H, m), 4.45–4.41 (1H, m), 4.13–4.09 (1H, dd), 3.51–3.49 (2H, dd), 3.11–3.03 (4H, m), 2.74–2.62 (3H, m), 2.32–2.27 (2H, m), 1.93–1.89 (2H, m), 1.71–1.63 (2H, m), 1.05–0.93 (6H, m).

EXAMPLE 51

[1S-[1α,2β,3β,4α(1S*,2R*)]]-2,3-Dihydroxy-N-[[3-(4-methoxyphenyl)propyl]amino]-4-[7-[(2-phenylcyclopropyl)amino]-5-(propylthio)-3H-1,2,3-triazolo [4,5-d]pyrimidin-3-yl]-cyclopentanecarboxamide a) [3aR-[3aα,4α,6α(1R*,2S*),6aα]]-Tetrahydro-N-[[3-(4-methoxyphenyl)propyl]amino]-6-[7-[(2-phenylcyclopropyl)amino]-5-(propylthio)-3H-1,2,3-triazolo[4,5-d]pyrimidin-3-yl]-2,2-dimethyl-4H-cyclopenta-1,3-dioxole-4-carboxamide The subtitle compound was prepared according to the method of example 50, step a) using the product of example 7, step d) and 3-(4-methoxyphenyl)propyl)amine (Prepared as described by K Fujimura etal, Bioorganic Medicinal Chemistry, 1997, 5, 1675).

MS (APCI) 570 (M+H+, 100%).

b) [1S-[1α,2β,3β,4α(1S*,2R*)]]-2,3-Dihydroxy-N-((3-(4-methoxyphenyl)propyl)amino]-4-[7-[(2-phenylcyclopropyl)amino]-5-(propylthio)-3H-1,2,3-triazolo[4,5-d]pyrimidin-3-yl]-cyclopentanecarboxamide The title compound was prepared according to the method of example 39, step b) using the product of step a).

Mpt 205–207° C.

MS (APCI) 530 (M+H+, 100%).

NMR δH (d$_6$-DMSO) 9.02 (1H, t), 7.91–7.90 (1H, t) 7.15–6.81 (4H, m), 5.12–4.93 (3H, m), 4.45–4.41 (1H, m), 4.134.09 (1H, dd), 3.73 (1H, s), 3.51–3.49 (2H, dd), 3.11–3.03 (4H, m), 2.73–2.56 (3H, m), 2.32–2.24 (2H, m), 1.91–1.86 (2H, m), 1.71–1.63 (2H, m), 1.05–0.94 (6H, m).

EXAMPLE 52

[1S-(1α,2β,3β,4α)]-N-Ethyl-2,3-dihydroxy-4-[7-[2-[(4-phenoxyphenyl)-ethyl]amino]-5-(propylthio)-3H-1,2,3-triazolo[4,5-d]pyrimidin-3-yl]-cyclopentanecarboxamide The title compound was prepared according to the method of Example 7, step e) using 2-(4-phenoxyphenyl)ethylamine.

Mpt 240–1° C.

MS (APCI) 578 (M+H+, 100%).

NMR δH (d$_6$-DMSO) 8.70 (1H, t), 7.90 (1H, t), 7.40–7.20 (4H, ABq), 7.20–6.90 (5H, m), 5.11 (1H, d), 4.98 (1H, d), 4.95 (1H, m), 4.42 (1H, m), 4.11 (1H, m), 4.09–3.73 (2H, m), 3.10–2.90 (6H, m), 2.73 (1H, m), 2.27 (2H, m), 1.70 (2H, m,), 1.70 (2H, m), 0.98 (6H, m).

EXAMPLE 53

[1S-(1α,2β,3β,4β)]-4-[7-[2-[(1,3-Benzodioxol-5-yl)ethyl]amino]-5-(propylthio)-3H-1,2,3,-triazolo[4,5d]pyrimidin-3-yl]-N-ethyl-2,3-dihydroxy-cyclopentanecarboxamide The title compound was prepared according to the method of Example 7, step e) using 2-(1,3-benzodioxol-5-yl)ethylamine hydrochloride.

Mpt 201–2° C.

MS (APCI) 530 (M+H+, 100%).

NMR δH (d₆-DMSO) 8.65 (1H, t), 7.92 (1H, t), 6.91–6.67 (3H, m), 5.96 (2H, s), 4.96 (1H, m), 4.92 (2H, m), 4.40 (1H, m), 4.11 (1H, m), 3.67 (2H, m), 3.08 (4H, m), 2.85 (2H, t), 2.70 (1H, m), 2.30 (2H, m), 1.71 (2H, m), 1.00 (6H, m).

EXAMPLE 54

[1S-(1α,2β,3β4α)]-N-Ethyl-2,3-dihydroxy-4 -[7-[(3-phenylprop-2-enyl)amino]-5-(propylthio)-3H-1,2,3-triazolo[4,5-d]pyrimidin-3-yl]-cyclopentanecarboxamide The title compound was prepared according to the method of example 7, step e) using the product of example 7, step d) and cinnamylamine (prepared as described by C. Moody et al J. Org. Chem. 1992, 57, 2105) followed by deprotection according to the method of example 18, step b). Purification (SiO₂, 0–10% methanol in ethyl acetate as eluant) afforded the title compound.

Mpt 222–224° C.

MS (APCI) 498 (M+H⁺, 100%).

NMR δH (d₆-DMSO) 9.26 (1H, t), 7.92 (1H, t), 7.40 (2H, d), 7.31 (2H, t), 7.22 (1H, t), 6.60–6.55 (1H, m), 6.42–6.36 (1H, m), 5.12 (1H, d), 4.99–4.94 (2H, m), 4.46–4.41 (1H, m), 4.30 (2H, t), 4.11 (1H, q), 3.16–3.05 (5H, m), 2.77–2.71 (1H, m), 2.37–2.20 (2H, m), 1.74–1.65 (2H, m), 1.07–0.94 (5H, m).

(EXAMPLE 55

[1S-[1α,2β,3β,4α(1S*,2R*)]]-[4-[7-[[2-(3,4-Difluorophenyl)cyclopropyl]amino]-5-(propylthio)-3H-1,2,3-triazolo[4,5-d]pyrimidin-3-yl]-N-ethyl-2,3-dihydroxy-cyclopentanecarboxamide a) [3aS-[1(E), 3aα,6α,7aβ]]-1-[3-3,4-Difluorophenyl)-1-oxo-2-propenyl]-hexahydro-8,8-dimethyl-3H-3a,6-methano-2,1-benzisothiazole-2,2-dioxide The subtitle compound was prepared according to the method of Example 34, step (a) using 3-(3,4-difluorophenyl)-2-propenoic acid.

MS (APCI) 382 (M+H⁺, 100%)

b) [3aS-[1(1S*,2S*),3aα,6α,7aβ]]-1-[[2-(3,4-Difluorophenyl))cyclopropyl]carbonyl]-hexahydro-8,8-dimethyl-3H-3a,6-methano-2,1-benzisothiazole-2,2-dioxide The subtitle compound was prepared according to the method of Example 34, step (b) using the product of step (a).

MS (APCI) 396 (M+H⁺, 100%)

c) (1R-trans)-2-(3,4-Difluorophenyl)-cyclopropanecarboxylic acid

The subtitle compound was prepared according to the method of Example 34, step (c) using the product of step (b).

NMR δH (CDCl₃) 7.68 (1H, dd, J=10.0, J=8.5 Hz), 7.46–7.31 (2H, m), 3.12–3.03 (1H, m), 2.37 (1H, dt, J=8.5, J=4.4 Hz), 2.17 (1H, dt, J=9.2,J=4.8 Hz), 1.86 (1H, ddd, J=8.5, J=6.9, J=5.2 Hz).

d) (1R -trans)-2-(3,4-Difluorophenyl)cyclopropanamine, [R-(R*,R*)]-2,3-dihydroxyhybantanedioate (1:1)

The subtitle compound was prepared according to the method of Example 7, step (b) using the product of step (c).

NMR δ(d₆-DMSO) 7.37–7.24 (1H, m), 7.23–7.17 (1H, m), 7.16–6.98 (1H, m), 3.97 (2H, s), 2.72–2.52 (1H, m), 2.21–2.14 (1H, m), 1.29–1.22 (1H, m), 1.17–1.11 (1H, m)

e) [1S-[1α,2β,3β,4α(1S*,2R*)]]-[4-[7-[[2-(3,4-Difluorophenyl)cyclopropyl]amino]-5-(propylthio)-3H-1,2,3-triazolo[4,5-d]pyrimidin-3-yl]-N-ethyl-2,3-dihydroxy-cyclopentaecarboxamide The title compound was prepared according to the method of Example 7, step (e) using the products of step (d) and Example 7, step (d).

NMR δH (d₆-DMSO) 9.37 (1H, s), 7.95–7.91 (1H, m), 7.36–7.27 (2H, m), 7.09–7.06 (1H m), 5.14–5.12 (1H, m), 5.00–4.94 (2H, m), 4.44–4.42 (1H, m), 4.11–4.09 (1H, m) 3.20–3.07 (3H, m), 2.96–2.86 (2H, m), 2.74–2.72 (1H, m), 2.33–2.24 (2H, m), 2.13–2.12 (1H, m), 1.57–1.47 (3H, m), 1.41–1.23 (1H, m), 1.05–1.00 (3H, t), 0.84–0.80 (3H, t),

MS (APCI) 534 (M+H⁺, 100%)

EXAMPLE 56

[1S-[1α,2β,3β,4α(1S*,2R*)]]-2,3-Dihydroxy-N-(3-methoxypropyl)-4-[7-[(2-phenylcyclopropyl)amino]-5-(propylthio)-3H-1,2,3-triazolo[4,5d]pyrimidin-3-yl]-cyclopentanecarboxamide The title compound was prepared according to the method of example 1, step d), using the product of example 1, step c) and 3-methoxy-1-propylamine, followed by the method of example 1, step e).

Mpt 171–173° C.

MS (APCI) 542 (M+H⁺, 100%).

MMR δH (d₆-DMSO) 9.35 (1H, d), 7.94(1H, s), 7.29 (2H, t), 7.20–7.16 (3H, m), 5.12 (1H, d), 4.984–4.89 (2H, m), 4.42 (1H, q), 4.11 (1H, q), 3.32 (2H, t), 3.21 (4H, s), 3.11 (2H, q), 2.90–2.83 (2H, m), 2.80–2.74 (1H, m), 2.33–2.21 (2H, m), 2.13 (1H, s), 1.64 (2H, quin), 1.53–1.46 (3H, m), 1.35–1.30 (1H m), 0.81 (3H, t).

EXAMPLE 57

[1S-[1α,2β,3β4α(E)]]-N-Ethyl-2,3-dihydroxy-4-[7-[(4-phenylbut-3-enyl)amino]-5-(propylthio)-3H-1,2, 3-triazolo[4,5d]pyrimidin-3-yl] cyclopentanecarboxamide a) [3aR-[3aα,4α,6α(E),6aα]]-N-Ethyl-tetrahydro-2,2-diethyl-6-[7-[(4-phenylbut-3-enyl)amino]-5-(propylthio)-3H-1,2,3-triazolo[4,5-d]pyrimidin-3-yl]-4H-cyclopenta-1,3-dioxole-4-carboxamide Prepared according to the method of example 50, step a) using the product of example 7, step d) and 4-phenylbut-3-enylamine (prepared as described by Imada J. Organomet. Chem. 1993, 451, 183).

MS (APCI) 552 (M+H⁺, 100%).

b) [1S-[1α,2β,3β,4α(E)]]-N-Ethyl-2,3-dihydroxy-4-[7-[(4-phenylbut-3-enyl)amino]-5-(propylthio)-3H-1,2,3-triazolo [4,5d]pyrimidin-3-yl]-cyclopentanecarboxamide The title compound was prepared according to the method of example 18, step b) using the product of step a).

Mpt 217° C.

MS (APCI) 512 (M+H⁺, 100%).

NMR δH (d₆-DMSO) 9.08 (1H, t), 7.92 (1H, t), 7.39–7.20 (5H, m), 6.48 (1H, d), 6.33 (1H, dt), 5.11 (1H, d), 4.98–4.94 (2H, m), 4.46–4.40 (1H, m), 4.13–4.09 (1H, m), 3.65 (1H, br q), 3.14–3.05 (4H, m), 2.78–2.70 (1H, m), 2.58–2.50 (3H, m), 2.32–2.25 (2H, m), 1.75–168 (2H, m), 1.05–0.96 (6H, m).

EXAMPLE 58

[1S-(1α,2β,3β,4α)]-N-Ethyl-2,3-dihydroxy-4-[7-[[3-(4-methylphenyl)propyl]amino]-5-(propylthio)-3H-2,3-triazolo[4,5-d]pyrimidin-3-yl]-cyclopentanecarboxamide a) [3aR-(3aα,4α,6α,6aα)]-N-Ethyl-tetrahydro-2,2-dimethyl-6-[7-[[3-(4-methylphenyl)propyl]amino]-5-(propylthio)-1,2,3-triazolo[4,5-d]pyrimidin-3-yl]-4H-cyclopenta-1,3-dioxole-4-carboxamide Prepared according to the method of example 50, step a) using the product of example 7, step d) and 3-(4- methylphenyl)propylamine (prepared as described by Braun, Chem. Ber. 1927, 60, 107).

MS (APCI) 554 (M+H$^+$, 100%).

b) [1S-(1α,2β,3β,4α)]-N-Ethyl-2,3-dihydroxy-4-[7-[[3-(4-methylphenyl)propyl]amino]-5-(propylthio)-3H-1,2,-triazolo[4,5-d]pyrimidin-3-yl]-cyclopentanecarboxamide The title compound was prepared according to the method of example 39, step b) using the product of step a).

Mpt 215° C.

MS (APCI) 514 (M+H$^+$, 100%).

NMR δH (d$_6$-DMSO) 9.03 (1H, t), 7.90 (1H, t), 7.13–7.06 (4H, m), 5.11 (1H, d), 4.98–4.93 (2H, m), 4.45–4.41 (1H, m), 4.13–4.09 (1H, m), 3.50 (2H, br q), 3.12–3.03 (4H, m), 2.74–258 (3H, m), 2.33–2.25 (2H, m), 2.25 (3H, s), 1.93–1.87 (2H, m), 1.75–1.61 (2H, m), 1.05–0.95 (6H, m).

EXAMPLE 59

[1S-[1α,2β,3β,4α(1S*,2M*)]]-N-Ethyl-2-dihydroxy-4-[7-[[2-(4-aminosulfonylphenyl)-cyclopropyl]amino]-5-(propylthio)-3H-1,2,3-triazolo[4,5-d]pyrimidin-3-yl]-cyclopentanecarboxamide a) (1S-trans)-4-(2-Aminocyclopropyl)phenylsulfonamide, hydrochloride The sub-title compound was prepared from (1R-trans)-phenylcyclopropanamine according to the method described in U.S. Pat. No. 3,487,154.

m.p. 211–2° C.

NMR δH (d$_6$-DMSO) 8.71 (3H, s), 7.72 (2H, d), 7.35 (2H, d), 7.33 (2H, s), 2.94–2.82 (1H, q). m), 2.47–2.42 (1H, m), 1.55–1.47 (1H, m), 1.28 (1H, q).

b) [1S-[1α,2β,30β,4α(1S*,2R*)]]-N-Ethyl-2,3-dihydroxy-4-[7-[[2-(4-aminosulfoylphenyl)-cyclopropyl]amino-]5-(propylthio)-3H1,2,3-triazolo[4,5-d]pyrimidin-3-yl]-cyclopentanecarboxamide The title compound was prepared according to the method of example 7, step (e) using the products of step (a) and example 7, step (d).

MS (APCI) 577 (M+H$^+$, 100%)

NMR δH (d$_6$-DMSO) 9.40 (1H, d), 7.91 (1H, t), 7.73 (2H, d), 7.38 (2H, d), 7.28 (2H, s), 5.13 (1H, s), 4.96 (2H, q), 4.43 (1H, t), 4.10 (1H, t), 3.32–3.30 (1H, m), 3.15–3.04 (2H, m), 2.98–2.80 (2H, m), 2.78–2.69 (1H, m), 2.37–2.17 (3H, m), 1.74–1.39 (4H, m), 1.03 3H, t), 0.82 (3H, t).

EXAMPLE 60

[1S-[1α,2β,3β,4α(1S*,2R*)]]-2,3-Dihydroxy-N-[[3-(4-trifluoromethylphenyl)propyl]amino]-4-[7-[(2-phenylcyclopropyl)amino]-5-(propylthio)-3H-1,2,3-triazolo[4,5-d]pyrimidin-3-yl]-cyclopentanecarboxamide a) [3aR-[3aα,4α,6α(1R*,2S*),6aα]]-Tetrahydro-2,2-dimethyl-N-[[3-(4-trifluoromethylphenyl)propyl]amino]-6-[7-[(2-phenylcyclopropyl)amino]-5-) propylthio)-3H-1,2,3-triazolo[4,5-d]pyrimidin-3-yl]-4H-cyclopenta-1,3dioxole-4-carboxamide Prepared according to the method of example 50, step a) using the product of example 1, step d) and 3-(4-trifluoromethylphenyl)propyl)amine (Prepared as describe by K. Fujimura etal, Bioorganic Medicinal Chemistry, 1997, 5, 1675).

MS (APCI) 608 (M+H$^+$, 100%).

b) [1S-[1α,2β,3β, 4α(1S*,2R*)]]-2,3-Dihydroxy-N-((3-(4-trifluoromethylphenyl)propyl)amino)-4-[7-[(2-phenylcyclopropyl)amino]-5-(propylthio)-3H-1,2,3-triazolo[4,5-d]pyrimidin-3-yl]-cyclopentanecarboxamide The title compound was prepared according to the method of example 39, step b) using the product of step a).

Mpt 215–217° C.

MS(APCI) 568(M+H$^+$, 100%)

NMR δH (d$_6$-DMSO) 9.06–9.03 (1H, t), 7.93–7.90 (1H, t), 7.64–7.45 (4H, m), 5.10–4.90 (3H, m), 4.41 (1H, m), 4.11–4.09 (1H, dd), 3.14–3.01 (4H, m), 2.78–2.69 (3H, m), 2.36–2.20 (2H, m), 1.99–1.94 (2H, m), 1.69–1.62 (2H, m), 1.04–0.94 (6H, m).

EXAMPLE 61

[1S-(1α,2β,3β,5α)]-4-[7-(Cyclopropylamino)-5-(2-naphthalenylthio)-3H-1,2,3-triazolo[4,5-d]pyrimidin-3yl]-N-ethyl-2,3-dihydroxy-4-cyclopentanecarboxamide The title compound was prepared according to the method of example 47 using 2-mercaptonaphthalene.

Mpt 182–4° C.

MS (APCI) 506 (M+H$^+$, 100%).

NMR δH (d$_6$-DMSO) 9.14 (1H, d), 8.22 (2H, m), 7.98–7.56 (6H, m), 5.11–5.09 (1H, d), 4.95–4.85 (1H, m), 4.38–36 (1H, m), 4.05–4.03 (1H, m), 3.11–3.07 (2H, m), 2.73–2.60 (2H, m), 2.27–2.11 (2H, m), 1.02 (3H, t), 0.86–0.41 (4H, m).

EXAMPLE 62

[1S-[1α,2β,3β,4α(1S*,2R*)]]-N-Ethyl-4-[5-(4-fluorophenylthio)-7-[(2-phenylcycloproply)amino]-3H-1,2,3-triazolo[4,5-d]pyrimidin-3yl]-2,3-dihydroxy-cyclopentanecarboxamide a) [3aR-[3aα,4α,6α(1R*,2S*),6aα]]-N-tetrahydro-2,2dimethyl-6-[7-[(2-phenylcyclopropyl)amino]-5-(4-fluorophenylthio)-3H-1,2,3-triazolo[4,5-d]pyrimidin-3-yl]-4H-cyclopenta-1,3-dioxole-4-carboxamide Prepared according to the method of example 4, step b), using the product from example 20, step a) and 4-fluorothiophenol.

MS (APCI) 590 (M+H$^+$, 100%).

b) [1S-[1α,2β,3β,4α(1S*,2R*)]]-N-Ethyl-4-[5-(4-fluorophenylthio)-7-[(2-phenylcyclopropyl)amino]-3H-1,2,3-triazolo[4,5-d]pyrimidin-3-yl]-2,3-dihydroxy-cyclopentanecarboxamide Prepared according to the method of example 39, step b) using the product of step a).

Mpt 195° C.

MS (ACI) 550 (M+H$^+$, 100%).

NMR δH (d$_6$-DMSO) 935 (1H, d), 7.90 (1H, t), 7.63–7.58 (2H, m), 7.32–7.05(7H, m), 5.10 (1H, d), 4.95 (1H, d), 4.94–4.80 (1H, m), 4.05–4.02 (1H, m), 3.13–3.06 (3H, m), 2.75–2.70 (1H, m), 2.30–2.10 (3H, m), 1.42–1.38 (1H, m), 1.17–1.13 1H, m), 1.03 (3H, t).

EXAMPLE 63

[1S-[1α,2β,3β,4α(1S*,2R*)]]-N-(2-Fluoroethyl)-2,3-dihydroxy-4-[5-(methylthio)-7-[(2-phenylcyclopropyl)amino]-3H-1,2,3-triazolo[4,5d]pyrimidin-3yl]-cyclopentanecarboxamide a) [3aR-[3aα,4α,6α,6aα(1R*,2S*)]]-N-(2-Fluoroethyl)-tetrahydro-2,2dimethyl-6-[5-(methylthio)-7-[(2-phenylcyclopropyl)amino]-3H-1,2,3-triazolo[4,5-d]pyrimidin-3-yl]-4H-cyclopenta-1,3-dioxole-4-carboxamide The title compound was prepared according to the method of example 39, step a)using the product of example 20, step b).

MS (APCI) 528 (M+H$^+$, 100%).

b) [1S-[1α,2β,3β,4α(1S*,2R*)]]-N-(2-Fluoroethyl)-2,3-dihydroxy-4-[5-)methylthio)-7-[(2-phenylcyclopropyl)

amino]-3H-1,2,3-triazolo[4,5d]pyrimidin-3yl]-cyclopentanecarboxamide

The title compound was prepared according to the method of example 39, step b) using the product of step c).

Mpt 165–167 ° C.

MS (APCI) 488 (M+H+, 100%).

NMR δH (d$_6$-DMSO) 9.35 (1H, d), 8.23–8.21 (1H, t), 7.30–7.16 (5H, m), 5.15–4.90 (3H, m), 4.50–4.12 (4H, m), 3.42–3.41 (1H, m). 3.20–3.18 (1H, m), 2.84–2.79 (1H, m), 2.33(3H, s), 2.28–2.10 (2H, m), 1.51–1.31 (2H, m),

EXAMPLE 64

[1S-[1α,2β,3β,4α(1S*,2R*)]]-2,3-Dihydroxy-N-(2-methoxyethyl)-4-[5-(methylthio)-7-[(2-phenylcyclopropyl)amino]-3H-1,2,3-triazolo[4,5-d]pyrimidin-3-yl]-cyclopentanecarboxamide a) [3aR-[3aα,4α,6α,6aα(1R*,2S*)]]-tetrahydro-N-(2-methoxyethyl)-2,2dimethyl-6-[5-(methylthio)-7-[(2-phenylcyclopropyl)amino]-3H-1,2,3-triazolo[4,5-d]pyrimidin-3-yl]-4H-cyclopenta-1,3-dioxole-4-carboxamide The subtitle compound was prepared by the method of example 39, step a) using the product of example 20, step b) and methyoxyethylamine.

MS (APCI) 540 (M+H+, 100%).

b) [1S-[1α,2β,3β,4α(1S*,2R*)]]-2,3-Dihydroxy-N-(2-methyoxyethyl)-4-[5-(methylthio)-7-[(2-phenylcyclopropyl)amino]-3H-1,2,3-triazolo[4,5-d]pyrimidin-3-yl]-cyclopentanecarboxamide The title compound was prepared according to the method of example 39, step b) using the product of step a).

Mpt 180–183 ° C.

MS (APCI) 500 (M+H+, 100%).

NMR δH (d$_6$-DMSO) 9.35 (1H, d), 8.02–7.99 (1H, t), 7.30–7.16 (5H, m), 5.13–4.95 (3H, m), 4.43 (1H, m), 4.11 (1H, m), 3.36 (3H, m), 3.24–3.19 (4H, m), 2.82–2.76 (1H, m), 2.30(3H, s), 2.38–2.10 (2H, m), 1.51–1.30 (2H, m),

EXAMPLE 65

[1S-[1α,2β,3β,4α(1S*,2R*)]]-2,3-Dihydroxy-N-(1-methylethyl)-4-[5-(methylthio)-7-[(2-phenylcyclopropyl)amino]-3H-1,2,3-triazolo[4,5d]pyrimidin-3-yl]-cyclopentanecarboxamide The title compound was prepared according to the method of example 39, step a) using the product of Example 20, step b) and 1-methylethylamine.

MS (APCI) 484 (M+H+, 100%).

NMR δH (d$_6$-DMSO) 7.64 (1H, d), 7.20 (5H, m), 5.00 (1H, dd), 4.85 (1H, d), 4.66 (1H, d), 4.46 (1H, dd), 4.17 (1H, d), 3.87 (1H, m), 2.78 (1H, m), 2.41 (3H, s), 2.30(3H, m), 1.46 (1H, m), 1.30 (1H, dd), 1.10 (9H, m).

EXAMPLE 66

(AR-C 126459XX)

[1S-(1α,2β,3β,4α)]-N-Ethyl-2,3-dihydroxy4-[7-[[3-(3-nitrophenyl)propyl]amino]-5-(propylthio)-3H-1,2,3-triazolo[4,5-d]pyrimidin-3-yl]-cyclopentanecarboxamide is The title compound was prepared according to the method of example 7, step e) using the product of example 7, step d) and 3-(3-nitrophenyl)propylamine (prepared as described by Ingold, J. Chem. Soc., 1927, 813).

Mpt 188–190° C.

MS (APCI) 545 (M+H+, 100%).

NMR δH (d$_6$-DMSO) 9.04 (1H, t), 8.11 (1H, s), 8.04 (1H, dt), 7.91 (1H, t), 7.72 (1H, d), 7.57 (1H, t), 5.11 (1H, d), 4.98–4.94 (2H, m), 4.45–4.39 (1H, m), 4.11 (1H, d), 3.53 (2H, q), 3.12–3.02 (5H, m), 2.80 (2H, t), 2.78–2.71 (1H, m), 2.37–2.20 (2H, m), 2.05–1.95 (2H, m), 1.72–1.61 (2H, m), 1.05–0.93 (5H, m).

EXAMPLE 67

[1S-[1α,2β,3β,4α(1S*,2R*)]]-N-Ethyl-2,3-dihydroxy4-[7-[(2-phenylcyclopropyl)amino]-5-[(3,3,3-trifluoropropyl)thio]-3H-1,2,3-triazolo[4,5-d]pyrimidin-3-yl]-cyclopentanecarboxamide

[3aR-[3aα,4α,6α(1R*,2S*),6aα]]-N-Ethyl-tetrahydro-2,2-dimethyl-6-[7-[(2-phenylcyclopropyl)amino]-5-[(3,3,3-trifluoropropyl)thio]-3H-1,2,3-triazolo[4,5-d]pyrimidin-3-yl]-4H-cyclopenta-1,3-dioxole-4-carboxamide Sodium hydrosulfide hydrate (0.4 g) was added to a solution of the product of example 20 step b) (0.44 g) in dimethyl sulphoxide (20 ml) and the solution stirred at room temperature for 1.5 hours. Water (3 ml) was added and the mixture partitioned between ethyl acetate and aqueous hydrochloric acid. The organic phase was dried and concentrated. The residue was dissolved in dichloromethane (10 ml) then N,N-diisopropylethylamine (0.35 ml) and 3,3,3-trifluoroeiodopropane (0.18 g) added. After stirring at room temperature for 2 hours the reaction mixture was concentrated and the residue purified (SiO2, isohexane:ethyl acetate 3:2 as eluant) to afford the subtitle compound (0.15 g).

Ms (APCI) 2 (M+H+, 100%).

b) [1S-[1α,2β,3β,4α(1S*,2R*)]]-N-Ethyl-2,3-dihydroxy 4-[7-[(2-phenylcyclopropyl)amino]-5-[(3,3,3-trifluoropropyl)thio]-3H-1,2,3-triazolo[4,5-d]pyrimidin-3-yl]-cyclopentanecarboxamide Prepared according to the method of example 18, step b) using the product of step a).

Mpt 200° C.

MS (APCI) 552 (M+H+, 100%).

NMR δH (d$_6$-DMSO) 9.46 (1H, d), 7.94 (1H, t), 7.31–7.17 (5H, m), 5.13 (1H, d), 5.00–4.93 (2H, m), 4.48–4.42 (1H m), 4.12–4.05 (1H, m), 3.35–3.05 (5H, m), 2.80–2.71 (1H, m), 2.60–2.45 (2H, m), 2.38–2.17 (3H, m), 1.50–1.45 (1H m), 1.37–1.30 (1H, m), 1.02 (3H, t).

EXAMPLE 68

[1S-[1α,2β,3β,4α(1S*,2R*)]]-4-[5-(Butylthio)-7-[(2-phenylcyclopropyl)amino]-3H-1,2,3-triazolo[4,5-d]pyrimidin-3-yl]-N-ethyl-2,3-dihydroxy-cyclopentanecarboxamide The title compound was prepared according to the method of example 4, step b) using butanethiol.

MS (APCI) 512 (M+H+, 100%).

NMR δH (d$_6$-DMSO) (363K) 8.90 (1H, s), 7.60 (1H, t), 7.27 (2H, m), 7.20 (3H, m), 4.95 (1H, dd), 4.81 (1H, d), 4.64 (1H, d), 4.76 (1H, dd), 4.18 (1H, dd), 3.15 (3H, m), 3.00 (2H, m), 2.74 (1H, m), 2.40–2.20 (3H, m), 1.60–1.40 (3H, m), 1.40–1.23 (2H, m), 1.04 (3H, t), 0.85 (3H, t).

EXAMPLE 69

[1S-(1α,2β,3β,4α(1S*,2R*))]-N-Ethyl-2,3-dihydroxy4-[5-(propylthio)-7-[[2-(4-trifluoromethoxyphenyl)cyclopropyl]amino]-3H-1,2,3-triazolo[4,5-d]pyrimidin-3-yl]-cyclopentanecarboxamide a) [3aS-[1(E),3aα,6α,7aβ]]-Hexahydro-8,8-dimethyl-1-[1-oxo-2-propenyl-3-(4-trifluoromethoxyphenyl)]-3H-3a,6-methano-2,1-benzisothiazole-2,2-dioxide The subtitle compound was prepared according to the method of Example 34, step (a) using 3-(4-trifluoromethoxyphenyl)-2-propenoic acid.

MS (APCI) 430 (M+H⁺,100%)

b) [3aS-[1(1S*,2S*),3aα,6α,7aβ]]-Hexahydro-8,8-dimethyl-1-[[2-(4-trifluoromethoxyphenyl)cyclopropyl]carbonyl]-3H-3a,6-methano-2,1-benzisothiazole-2,2dioxide The subtitle compound was prepared according to the method of Example 34, step (b) using the product of step (a).

MS (APCI) 442 (M–EH⁺, 100%)

c) (1R-trans)-2-(4-Trifluoromethoxyphenyl)-cyclopropanecarboxylic acid

The subtitle compound was prepared according to the method of Example 34, step (c) using the product of step (b).

MS (APCI) 245 (M–H⁺,100%)

d) (1R-trans)-2-(4-Trifluoromethoxyphenyl)cyclopropanamine, [R-(R*,R*)]-2,3-dihydroxybutanedioate (1:1)

The subtitle compound was prepared according to the method of Example 7, step (b) using the product of step (c).

NMR δH (d₆-DMSO) 7.28–7.22 (4H, m), 3.95 (2H, s), 2.73–2.66 (1H, m), 2.19–2.13 (1H, m), 1.27–1.21 (1H, m), 1.17–1.11(1H, m)

e) [3aR-[3aα,4α,6α(1R*,2S*),6aα]]-Tetrahydro-2,2-dimethyl-N-methyl-6-[5-(propylthio)-7-[[2-(4-trifluoromethoxyphenyl)cyclopropyl]amino]-3H-1,2,3-triazolo[4,5-d]pyrimidin-3-yl]-4H-cyclopenta-1,3-dioxole-4-carboxamide The subtitle compound was prepared according to the method of Example 1, step (c) using the product of step (d).

MS (APCI) 636 (M+H⁺,100%)

f) [1S-(1α,2β,3β,4α(1S*,2R*))]-N-Ethyl-2,3-dihydroxy-4-[5-(propylthio)-7-[[2-(4-trifluoromethoxyphenyl)cyclopropyl]amino]-3H-1,2,3-triazolo[4,5-d]pyrmdin-3-yl]-cyclopentanecarboxamide The tide compound was prepared according to the method of Example 18, step (b) using the product of step (e).

MS (APCI) 582 (M+H⁺,100%)

NMR δH (d₆-DMSO)9.38 (1H, s),7.97–7.26 (4H, m), 5.12 (1H, s). 5.00–4.91 (2H, m), 4.42 (1H, s), 4.10 (1H, s), 3.32 (1H, m), 3.09 (2H, q), 2.97–2.85 (2H, m),2.83–2.73 (1H, m), 2.37–1.85 (3H, m), 1.48–1.36 (4H, m), 1.02 (3H, t), 0.77 (3H, t)

EXAMPLE 70

[1S-[1α,2β,3β,4α(1S*,2R*)]]-2,3-Dihydroxy-N-(2-methoxyethyl)-N-methyl-[4-[7-[(2-phenylcyclopropyl)amino]-5-(propylthio)-3H-1,2,3-triazolo[4,5-d]pyrimidin-3-yl]-cyclopentanecarboxamide The title compound was prepared according to the method of example 39, step a) using the product of example 1, step c) and (2-methyoxyethyl)methylamine (prepared as described by J. Hine et al. J. Am. Chem. Soc. 1975, 97, 6513) followed by deprotection according to the method of example 39, step b). Purification (supercritical fluid chromatography, NC100-7Diol Hichrom column, 5–30% methanol in carbon dioxide over 25 minutes as eluant) afforded the title compound.

Mpt 85–95° C.

MS (APCI) 542 (M+H⁺,100%.

NMR δH (d₆DMSO)9.35 (1H, d), 7.31–7.26 (2H, m), 7.21–7.15 (3H, m), 5.15–4.99 (3H, m), 4.50–4.40 (1H, m), 4.14–4.08 (1H, m), 3.75–3.65 (1H, m), 3.50–3.43 (4H, m), 3.30–3.10 (4H, m), 3.08 (1H, s), 2.99–2.93 (1H, m), 2.80 (2H, s), 2.37–2.20 (2H, m), 2.18–2.10 (1H, m), 1.53–1.46 (3H, m), 1.36–1.29 (1H, m), 0.88–0.79 (4H, m).

EXAMPLE 71

[1S-[1α,2β,3β,4α(1S*,2R*)]]-N-(4-Cholorophenyl)-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide a) [3aR-[3aα,4α,6α(1R*,2S*),6aα]]-N-(4-Chlorophenyl)-tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxamide The subtitle compound was prepared according to the method of example 39, step a) using the product of example 1, step c) and 4-chlorolphenylamine.

MS (APCI) 620 (M+H⁺, 100%).

b) [1S-[1α,2β,3β,4α(1S*,2R*)]]-N-(4Chlorophenyl)-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide The tide compound was prepared according to the method of example 39, step b) using the product of step a).

Mpt 207–209° C.

MS (APCI) 580 (M+H⁺, 100%).

NMR δH (d₆-DMSO) 10.22(1H, s), 9.35 (1H, d), 7.69–7.15 (9H, m), 5.26–5.18 (2H, m), 5.02–5.00 (1H, m), 4.47–4.43 (1H, m), 4.27–4.25(1H, m), 3.21–3.18 (1H, m), 3.01–2.83 (3H, m), 2.45–2.27 (2H, m), 2.13–2.10 (1H, m), 1.55–1.31(4H, m), 0.83–0.78 (3H, t).

EXAMPLE 72

[1S-[1α,2β,3β,4α(1S*,2R*)]]-N-(2H-1,3-Benzodioxol-5-ylmethyl)-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide a) [3aR-[3aα,4α,6α(1R*,2S*),6aα]]-N-(2H-1,3-Benzodioxol-5-ylmethyl)-tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxamide The subtitle compound was prepared according to the method of example 39 step a) using the product of example 1, step c) and 2H-1,3-benzodioxol-5-ylmethylamine.

MS (APCI) 644 (M+H⁺, 100%).

b) [1S-[1α,2β,3β,4α(1S*,2R*)]]-N-(2H-1,3-Benzodioxol-5-ylmethyl)-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide The title compound was prepared according to the method of example 39, step b) using the product of step a).

Mpt 182–185° C.

MS (APCI) 604 (M+H⁺, 100%).

NMR δH (d₆-DMSO) 9.35 (1H, d), 8.40 (1H, t), 7.31–7.15 (5H, m), 6.85–6.71 (3H, m), 5.97 (2H, s), 5.16–4.95 (3H, m), 4.44–4.42 (1H, m), 4.22–4.13 (3H, m), 3.18–3.16 (1H, m), 2.94 (1H, m), 2.86–2.81 (2H, m), 2.37–2.27 (2H, m), 2.13 (1H, m), 1.53–1.31(4H, m), 0.82–0.78 (3H, t).

EXAMPLE 73

[1S-[1α,2β,3β,4α(1S*,2R*)]]-N-(3-Chorophenylmethyl)-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide a) [3aR-[3aα,4α,6α(1R*,2S*),6aα]]-N-(3-Chlorophenylmethyl)-tetrahydro-2,2-dimethyl-6-[7-[(2- phenylcyclopropyl)amino]-5-(propylthio)-3H-1,2,3-triazolo[4,5-d]pyrimidin-3-yl]-4H-cyclopenta-1,3-dioxole-4-carboxamide The subtitle compound was prepared according to the method of example 39, step a) using the product of example 1, step c) and 3-chlorobenzylamine.

MS (APCI) 635 (M+H$^+$, 100%).

b) [1S-[1α,2β,3β,4α(1S*,2R*)]]-N-(3-Chlorophenylmethyl)-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide The title compound was prepared according to the method of example 39, step b) using the product of step a).

Mpt 178–180° C.

MS (APCI) 595 (M+H$^+$, 100%).

NMR δH (d$_6$-DMSO) 9.36 (1H, d), 8.56–8.52 (1H, t), 7.38–7.15 (9H, m), 5.20–4.97 (3H, m), 4.46–4.15 (4H, m), 3.21–3.20 (1H, m), 2.96 (1H, m), 2.86–2.81 (2H, m), 2.37–2.27 (2H, m), 2.13 (1H, m), 1.54–1.31(4H, m), 0.82–0.77 (3H, t).

EXAMPLE 74

[1S-[1α,2β,3β,4α(1S*,2R*)]]-N-Ethyl-4-[5-(ethylthio)-7-[(2-phenylcyclopropyl)amino]-3H-1,2,3-triazolo[4,5-d]pyrimidin-3-yl]-2,3-dihydroxy-cyclopentanecarboxamide The title compound was prepared according to the method of example 4, step b) using ethanethiol.

MS (APCI) 484 (M+H$^+$, 100%).

NMR δH (d$_6$-DMSO) (363K) 9.36 (1H, d), 7.93 (1H, t), 7.28 (2H, t), 7.18 (3H, m), 5.11 (1H, d), 4.99 (2H, m), 4.41 (1H, dd), 4.09 (1H, dd), 3.20 (1H, m), 3.15 (2H, m), 2.90–2.80 (2H, m), 2.80–2.70 (1H, m), 2.40–2.20 (2H, m), 2.15 (1H, m), 1.55 (1H, m), 1.30 (2H, m), 1.06 (3H, t), 1.02 (3H, t).

EXAMPLE 75

[1S-(1α,2β, 3β, 4α)]-4-[7-[(Cyclopropyl)amino]-5-(propylthio)-3H-1,2,3-triazolo[4,5-d]pyrimidin-3-yl]-2,3-dihydroxy-N-(1,1-dimethyl-2-phenylethyl)cyclopentanecarboxamide a) [3aR-(3aα,4α,6α,6aα)]-6-[7-(Cyclopropylamino)-5-(propylthio)-3H-1,2,3-triazolo[4,5-d]pyrimidin-3-yl]-tetrahydro-2,2-dimethyl-4H-cyclopenta-1,3-dioxole-4-carboxylic acid Prepared according to the method of example 50, step a) using the product of example 1, step b) and cyclopropylamine.

MS (APCI) 435 (M+H$^+$, 100%).

b) [3aR-(3aα,4α,6α,6aα)]-6-[7-[(Cyclopropyl)amino]-5-(propylthio)-3H-1,2,3-triazolo[4,5-d]pyrimidin-3-yl]-N-(1,1-Dimethyl-2-phenylethyl)-2,2-dimethyl-tetrahydro-4H-cyclopenta-1,3-dioxole-4-carboxamide The subtitle compound was prepared according to the method of example 39, step a) using the product of example 75, step a) and 1,1-dimethyl-2-phenylethylamine.

MS (APCI) 566 (M+H$^+$, 100%).

c) [1S-(1α,2β,3β,4α)]-4-[7-[(Cyclopropyl)amino]-5-(propylthio)-3H-1,2,3-triazolo[4,5-d]pyrimidin-3-yl]-2,3-dihydroxy-N-(1,1-dimethyl-2-phenylethyl)cyclopentanecarboxamide The title compound was prepared according to the method of example 39, step b) using the product of step b).

Mpt 110–114° C.

MS (APCI) 526 (M+H$^+$, 100%).

NMR δH (d$_6$-DMSO) 9.10–9.08 (1H, d), 7.33–7.10 (6H, m), 5.14–4.93 (3H, m), 4.49–4.48 (1H, m), 4.15 (1H, m), 3.32 (1H, m), 3.20–2.94 (5H, m), 2.79–2.74 (1H, m), 2.31–2.29 (2H, m), 1.76–1.68 (2H, m), 1.24–1.18 (6H, m), 0.82–0.69 (6H, m).

EXAMPLE 76

[1S-[1α,2β,3β,4α(1S*,2R*)]]-N-(3-Ethoxypropyl)-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide a) [3aR-[3aα,4α,6α(1R*,2S*),6aα]]-N-(3-Ethoxypropyl)-tetrahydro-2,2-dimethyl-6-[7-[(2-phenylcyclopropyl)amino]-5-(propylthio)-3H-1,2,3-triazolo[4,5-d]pyrimidin-3-yl]-4H-cyclopenta-1,3-dioxole-4-carboxamide The subtitle compound was prepared according to the method of example 39, step a) using the product of example 1, step c) and 3-ethoxypropylamine.

MS (APCI) 596 (M+H$^+$, 100%).

b) [1S-[1α,2β,3β,4α(1S*,2R*)]]-N-(3-Ethoxypropyl)-2,3-dihydroxy-4-[7-[(2-phenylcyclopropyl)amino]-5-(propylthio)-3H-1,2,3-triazolo[4,5-d]pyrimidin-3-yl]-cyclopentanecarboxamide The title compound was prepared according to the method of example 39, step b) using the product of step a).

Mpt 168–170° C.

MS (APCI) 556 (M+H$^+$, 100%).

NMR δH (d$_6$-DMSO) 9.35–9.34 (1H, d), 7.93–7.90 (1H, t), 7.30–7.15 (5H, m), 5.18–4.90 (3H, m), 4.40 (1H, m), 4.10 (1H, m), 3.42–3.15 (5H, m), 3.09–2.67 (6H, m), 2.36–2.10 (3H, m), 1.71–1.29 (5H, m), 1.11–1.07 (3H, t), 0.82–0.79 (3H, t).

EXAMPLE 77

[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-N-propyl-cyclopentanecarboxamide.

a) [3aR-[3aα,4α,6α(1R*,2S*),6aα]]-Tetrahydro-2,2-dimethyl-6-[7-[(2-phenylcyclopropyl)amino]-5-(propylthio)-3H-1,2,3-triazolo[4,5-d]pyrimidin-3-yl]-N-propyl-4H-cyclopenta-1,3-dioxole-4-carboxamide The subtitle compound was prepared according to the method of example 39, step a) using the product of example 1 step c) and propylamine.

MS (APCI) 552 (M+H$^+$, 100%).

b) [1S-[1α,2β,3β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-N-propyl-cyclopentanecarboxamide The title compound was prepared according to the method of example 39, step b) using the product of step a).

Mpt 184–186° C.

MS (APCI) 512 (M+H$^+$, 100%).

NMR δH (d$_6$-DMSO) 9.35–9.34 (1H, d), 7.92–7.89 (1H, t), 7.30–7.15 (5H, m), 5.10–4.90 (3H, m), 4.40 (1H, m), 4.10 (1H, m), 3.20–2.73 (6H, m), 2.36–2.10 (3H, m), 1.54–1.29 (6H, m), 0.86–0.79 (6H, m).

EXAMPLE 78

[1S-[1α,2β,3β,4α(1S*,2R*)]]-N-(3-Ethoxypropyl)-2,3dihydroxy-4-[5-(methylthio)-7-[(2-phenylcyclopropyl)amino]-3H-1,2,3-triazolo[4,5-d]pyrimidin-3-yl]-cyclopentanecarboxamide a) [3aR -[3aα,4α,6α(1R*,2S*),6aα]]-N-(3-Ethoxypropyl)-tetrahydro-2,2-dimethyl-6-[5-(methylthio)-7-[(2- phenylcyclopropyl)amino]-3H-1,2,3-triazolo[4,5-d]pyrimidin-3-yl]-4H-cyclopenta-1,3-dioxole-4-carboxamide The subtitle compound was prepared according to the method of example 39, step a) using the product of example 20, step b) and 3-ethyoxypropylamine.

MS (APCI) 568 (M+H$^+$, 100%).

b) [1S-[1α,2β,3β,4α(1S*,2R*)]]-N-(3-Ethoxypropyl)-2,3-dihydroxy-4-[5-(methylthio)-7-[(2-phenylcyclopropyl)amino]-3H-1,2,3-triazolo[4,5-d]pyrimidin-3-yl]-cyclopentanecarboxamide The title compound was prepared according to the method of example 39, step b) using the product of step a).

Mpt 171–173° C.

MS (APCI) 528 (M+H$^+$, 100%).

NMR δH (d$_6$-DMSO) 9.36–9.34 (1H, d), 7.92–7.90 (1H, t), 7.31–7.15 (5H, m), 5.14–4.96 (3H, m), 4.43–4.41 (1H, m), 4.12–4.11 (1H, m), 3.42–3.33 (6H, m), 3.19–3.08 (3H, m), 2.76–2.74 (1H, m), 2.36–2.13 (5H, m), 1.65–1.60 (2H, m), 1.34–1.32 (1H, m), 1.11–1.07 (3H, t)

EXAMPLE 79

[1S-[1α,2β,3β,4α(1S*,2R*)]]-2,3-Dihydroxy-4-[5-(methylthio)-7-[(2-phenylcyclopropyl)amino]-3H-1,2,3-triazolo[4,5-d]pyrimidin-3-yl]-N-propyl-cyclopentanecarboxamide a) [3aR-[3aα,4α,6α(1R*,2S*),6aα]]-Tetrahydro-2,2-dimethyl-6-[5-(methylthio)-7-[(2-phenylcyclopropyl)amino]-3H-1,2,3-triazolo[4,5-d]pyrimidin-3-yl]-N-propyl-4H-cyclopenta-1,3-dioxole-4-carboxamide The subtitle compound was prepared according to the method of example 39, step a) using the product of example 20, step b) and propylamine.

MS (APCI) 524 (M+H$^+$, 100%).

b) [1S-[1α,2β,3β,4α(1S*,2R*)]]-2,3-Dihydroxy-4-[5-(methylthio)-7-[(2-phenylcyclopropyl)amino]-3H-1,2,3-triazolo[4,5-d]pyrimidin-3-yl]-N-propyl-cyclopentanecarboxamide The title compound was prepared according to the method of example 39, step b) using the product of step a).

Mpt 167–169° C.

MS (APCI) 484 (M+H$^+$, 100%).

NMR δH (d$_6$-DMSO) 9.36–9.34 (1H, d), 7.92–7.89 (1H, t), 7.31–7.15 (5H, m), 5.00–4.93 (2H, m), 4.45–4.40 (1H, m), 4.13–4.10 (1H, t), 3.21–3.17 (1H, m), 3.06–3.00 (2H, m), 2.77–2.72 (1H, m), 2.36–2.11 (5H, m), 1.50–1.32(4H, m), 0.87–0.82 (3H, t)

EXAMPLE 80

[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-N-(2-pyridylmethyl)-cyclopentanecarboxamide a) [3aR-[3aα,4α,6α(1R*,2S*),6aα]]-Tetrahydro-2,2-dimethyl-6-[7-[(2-phenylcyclopropyl)amino]-5-(propylthio)-3H-1,2,3-triazolo[4,5-d]pyrimidin-3-yl]-N-(2-pyridylmethyl)-4H-cyclopenta-1,3-dioxole-4-carboxamide The subtitle compound was prepared according to the method of example 39, step a) using the product of example 1, step c) and 2-(aminomethyl)pyridine.

MS (APCI) 601 (M+H$^+$, 100%).

b) [1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-N-(2-pyridylmethyl)-cyclopentanecarboxamide The title compound was prepared according to the method of example 39, step b) using the product of step a).

Mpt 168–171° C.

MS (APCI) 561 (M+H$^+$, 100%).

NMR δH (d$_6$-DMSO) 9.35 (1H, d), 8.57–8.54 (1H, m), 8.49 (1H, m), 7.76–7.73 (1H, m), 7.30–7.15 (5H, m), 5.16–4.96 (3H, m), 4.46–4.35 (3H, m), 4.20–4.16 (1H, m), 3.23–3.21 (1H, m), 2.98–2.80 (3H, m), 2.44–2.27 (2H, m), 2.10 (1H, m), 1.54–1.29 (4H, m), 0.81–0.77 (3H, t).

EXAMPLE 81

[1S-[1α,2β,3β4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-N-(3-pyridylmethyl)-cyclopentanecarboxamide a) [3aR-[3aα,4α,6α(1R*,2S*),6aα]]-Tetrahydro-2,2dimethyl-6-[7-[(2-phenylcyclopropyl)amino]-5-(propylthio)-3H-1,2,3-triazolo[4,5-d]pyrimidin-3-yl]-N-(3-pyridylmethyl)-4H-cyclopenta-1,3dioxole-4carboxamide The subtitle compound was prepared according to the method of example 39, step a) using the product of example 1, step c) and 3-(aminomethyl)pyridine.

MS (APCI) 601 (M+H$^+$, 100%).

b) [1S-[1α,2β,3β,4α(1S*,2R*)]]-2,3-Dihydroxy-4-[7-[(2-phenylcyclopropyl)amino[-5-(propylthio)-3H-1,2,3-triazolo[4,5-d]pyrimidin-3-yl]-N-(3-pyridylmethyl)-cyclopentanecarboxamide The title compound was prepared according to the method of example 39, step b) using the product of step a).

Mpt 159–161° C.

MS (APCI) 561 (M+H$^+$, 100%).

NMR δH (d$_6$-DMSO) 9.34 (1H, d), 8.56–8.44 (3H, m), 7.67–7.65 (1H, m), 7.36–7.16 (6H, m), 5.16–4.96 (3H, m), 4.41–4.14 (4H, m), 3.21–2.92 (2H, m), 2.85–2.80 (2H, m),2.42–1.91 (3H, m), 1.54–1.29 (4H, m), 0.81–0.77 (3H, t).

EXAMPLE 82

[1S-[1α,2β,3β,4α(1S*,2R*)]]-2,3-Dihydroxy-4-[7-(2-phenylcyclopropyl)amino]-5-(propylthio)-3H-1,2,3-triazolo[4,5-d]pyrimidin-3-yl]-N-(4-pyridylmethyl)-cyclopentanecarboxamide a) [3aR-[3aα,4α,6α(1R*,2*),6aα]]-Tetrahydro-2,2-diethyl-6-[7-[(2-phenylcyclopropyl)amino]-5-(propylthio)-3H-1,2,3-triazolo[4,5-d]pyrimidin-3-yl]-N-(4-pyridylmethyl)-4H-cyclopenta-1,3-dioxole-4-carboxamide The subtitle compound was prepared according to the method of example 39, step a) using the product of example 1, step c) and 4-(aminomethyl)pyridine.

MS (APCI) 601 (M+H$^+$, 100%).

b) [1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-N-(4-pyridylmethyl)-cyclopentanecarboxamide The title compound was prepared according to the method of example 39, step b) using the product of step a).

Mpt 140–145° C.

MS (APCI) 561 (M+H$^+$, 100%).

NMR δH (d$_6$-DMSO) 9.35 (1H, d), 8.58–8.56 (1H, t), 8.48 (3H, m), 7.36–7.16 (7H, m), 5.16–4.94 (3H, m), 4.41–4.14 (4H, m), 3.21–3.19 (1H, m), 2.97–2.80 (3H, m), 2.45–2.10 (3H, m), 1.54–1.29 (4H, m), 0.81–0.78 (3H, t).

EXAMPLE 83

[1S-(1α,2β,3β,4α)]-4-(Butylamino)-5-(propylthio)-3H-1,2,3-triazolo[4,5-d]pyrimidin-3-yl]-2,3-dihydroxy-N-(4-pyridylmethyl)-cyclopentanecarboxamide Prepared according to the method of example 1, step d) using [1S-(1α,2β,3β,4α)]-4-[7-(butylamino)-5-

(propylthio)-3H-1,2,3-triazolo[4,5-d]pyrimidin-3-yl]-2,3-dihydroxycyclopentanecarboxylic acid (prepared as described in WO-09828300) and 4-(aminomethyl)pyridine.

Mpt 146–9° C.

MS (APCI) 501 (M+H$^+$, 100%).

NMR δH (d$_6$-DMSO) 9.00 (1H, t), 8.58 (1H, t), 8.50 (2H, d), 7.27 (2H, d), 5.18 (1H, br s), 5.07 (1H, br s), 5.02–4.95 (1H, m), 4.43–4.29 (3H, m), 4.20 (1H, br s), 3.49 (2H, q), 3.15–3.03 (2H, m), 2.92–2.87 (1H, m), 2.45–2.24 (2H, m), 1.73–1.56 (4H, m), 1.41–1.30 (2H, m), 0.97 (3H, t), 0.91 (3H, t).

EXAMPLE 84

[1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-N-(3-pyridyl)-cyclopentanecarboxamide a) [3aR-[3aα,4α,6α(1R*,2S*),6aα]]-Tetrahydro-2,2-dimethyl-6-[7-[(2-phenylcyclopropyl)amino]-5-(propylthio)-3H-1,2,3-triazolo[4,5-d]pyrimidin-3-yl]-N-(3-pyridyl)-4H-cyclopenta-1,3-dioxole-4-carboxamide The subtitle compound was prepared according to the method of example 39, step a) using the product of example 1, step c) and 3-aminopyridine.

MS (APCI) 587 (M+H$^+$, 100%).

b) [1S-[1α,2β,3β,4α(1S*,2R*)]]-2,3-Dihydroxy-4-[7-[(2-phenylcyclopropyl)amino]-5-(propylthio)-3H-1,2,3-triazolo[4,5-d]pyrimidin-3-yl]-N-(3-pyridyl)-cyclopentanecarboxamide The title compound was prepared according to the method of example 39, step b) using the product of step a).

MS (APCI) 547 (M+H$^+$, 100%).

NMR δH (d$_6$-DMSO) 10.32 (1H, s), 9.37 (1H, d), 8.80–8.79 (1H, m), 8.26–8.25 (1H, d), 8.10–8.07 (1H, d), 7.37–7.15 (6H, m), 5.29–5.21 (2H, m), 5.04–5.02 (1H, m), 4.47–4.43 (1H, m), 4.28–4.27 (1H, m), 3.20–2.80 (4H, m), 2.40–2.13 (3H, m), 1.54–1.31 (4H, m), 0.82–0.78 (3H, t).

EXAMPLE 85

[1S-(1α,2β,3β,4α)]-4-[7-(Butylamino)-5-(propylthio)-3H-1,2,3-triazolo[4,5-d]pyrimidin-3-yl]-N-ethyl-2,3-dihydroxy-N-(4-pyridylmethyl)-cyclopentanecarboxamide Prepared according to the method of example 1, step d) using [1S-(1α,2β,3β,4α)]-4-[7-(butylamino)-5-(propylthio)-3H-1,2,3-triazolo[4,5-d]pyrimidin-3-yl]-2,3-dihydroxycyclopentanecarboxylic acid (prepared as described in WO-09828300) and N-ethyl-4-(aminomethyl)pyridine.

Mpt 100° C.

MS (APCI) 529 (M+H$^+$, 100%).

NMR δH (d$_6$-DMSO) 8.99 (1H, t), 8.49 (2H, d), 7.20 (2H, d), 5.20–4.21 (6H, m), 3.53–3.27 (4H, m), 3.12–3.05 (2H, m), 2.51–2.24 (2H, m), 1.72–1.58 (4H, m), 1.39–1.31 (2H, m), 1.16–0.89 (9H, m).

EXAMPLE 86

[1S-(1α,2β,3β,4α)]-4-[7-(Butylamino)-5-(propylthio)-3H-1,2,3-triazolo[4,5-d]pyrimidin-3-yl]-2,3-dihydroxy-N-(3-pyridylmethyl)-cyclopentanecarboxamide Prepared according to the method of example 1, step d) using [1S-(1α,2β,3β,4α)]-4-[7-(butylamino)-5-(propylthio)-3H-1,2,3-triazolo[4,5-d]pyrimidin-3-yl]-2,3-dihydroxycyclopentanecarboxylic acid (prepared as described in WO-09828300) and 3-(aminomethyl)pyridine.

Mpt 200–1° C.

MS (APCI) 501 (M+H$^+$, 100%).

NMR δH (d$_6$-DMSO) 8.99 (1H, t), 8.50–8.44 (3H, m), 7.66 (1H, d), 7.34 (1H, dd), 5.16 (1H, d), 5.04–4.92 (2H, m), 4.50–4.25 (3H, m), 4.20–4.10 (1H, m), 3.50 (2H, q), 3.10–3.05 (2H, m), 2.90–2.80 (1H, m), 2.43–2.20 (2H, m), 1.70–1.58 (4H, m), 1.40–1.30 (2H, m), 0.97 (3H, t), 0.91 (3H, t).

EXAMPLE 87

[1S-(1α,2β,3β,4α)]-4-[7-(Butylamino)-5-(propylthio)-3H-1,2,3-triazolo[4,5-d]pyrimidin-3-yl]-2,3dihydroxy-N-methyl-N-(3-pyridylmethyl)-cyclopentanecarboxamide Prepared according to the method of example 1, step d) using [1S-(1α,2β,3β,4α)]-4-[7-(butylamino)-5-(propylthio)-3H-1,2,3-triazolo[4,5-d]pyrimidin-3-yl]-2,3-dihydroxycyclopentanecarboxylic acid (prepared as described in WO-09828300) and 3-(N-methylaminomethyl) pyridine.

Mpt 173° C.

MS (APCI) 515 (M+H$^+$, 100%).

NMR δH (d$_6$-DMSO) 8.99 (1H, t), 8.51–8.48 (2H, m), 7.64 (1H, d), 7.37 (1H, dd), 5.16 (1H, br s), 5.10–4.98 (1H, m), 4.59 (2H, q), 4.50–4.43 (1H, m), 4.20–4.16 (1H, m), 3.49 (2H, q), 3.30–3.24 (1H, m), 3.12–3.05 (2H, m), 3.05 (3H, s), 2.52–2.30 (2H, m), 1.73–1.58 (4H, m), 1.39–1.31 (2H, m), 1.01–0.89 (6H, m).

EXAMPLE 88

[1S-[1α,2β,3β,4α(1S*,2R*)]]-4-[7-[(Cyclopropyl)amino]-5-(propylthio)-3H 12,3 -triazolo[4,5-d]pyrimidin-3-yl]-2,3-dihydroxy-N-(4-pyridylmethyl)-cyclopentanecarboxamide a) [3aR-[3aα,4α,6α(1R*,2S*),6aα]]-Tetrahydro-2,2-dimethyl-6-[7-[(cyclopropyl)amino]-5-(propylthio)-3H-1,2,3-triazolo[4,5-d]pyrimidin-3-yl]-N-(4-pyridylmethyl)-4H-cyclopenta-1,3-dioxole-4-carboxamide The subtitle compound was prepared according to the method of example 39, step a) using the product of example 75, step a) and 4-(aminomethyl)pyridine.

MS (APCI) 525 (M+H$^+$, 100%).

b) [1S-[1α,2β,3β,4α(1S*,2R*)]]-4-[7-[(Cycopropyl)amino-5-(propylthio)-3H-1,2,3-triazolo[4,5-d]pyrimidin-3-yl]-2,3-dihydroxy-N-(4-pyridylmethyl)-cyclopentanecarboxamide The title compound was prepared according to the method of example 39, step b) using the product of step a).

Mpt 140–143° C.

MS (APCI) 485 (M+H$^+$, 100%).

NMR δH (d$_6$-DMSO) 9.08 (1H, d), 8.57 (1H, m), 8.49–8.48 (2H, m), 7.26–7.25 (2H, m), 5.19–4.96 (3H, m), 4.46–4.18 (4H, m), 3.18–3.04 (3H, m), 2.92–2.86 (1H, m), 2.45–2.24 (3H, m), 1.73–1.62 (2H, m), 1.02–0.68 (6H, m).

EXAMPLE 89

[1S-(1α,2β,3β,4α(1S*,2R*)]]-4-[7-[(Cyclopropyl)amino]-5-(propylthio)-3H-1,2,3-triazolo[4,5-d]pyrimidin-3-yl]-N-ethyl-2,3-dihydroxy-N-(4-pyridylmethyl)-cyclopentanecarboxamide a) [3aR-[3aα,4α,6α(1R*,2S*),6aα]]-6-[7-[(Cyclopropyl)amino]-5-(propylthio)-3H-1,2,3-triazolo[4,5-d]pyrimidin-3- yl]-N-ethyl-tetrahydro-2,2-diethyl-N-(4-pyridylmethyl)-4H-cyclopenta-1,3-dioxole-4carboxamide The subtitle compound was prepared according to the method of example 39 step a) using the product of example 75, step a) and 4-(ethylaminomethyl)pyridine.

MS (APCI) 553 (M+H$^+$, 100%).

b) [1S-[1α,2β,3β,4α(1S*,2R*)]]-4-[7-[(Cyclopropyl)amino]-5-(propylthio)-3H-1,2,3-triazolo[4,5-d]pyrimidin-3-yl]-N-ethyl-2,3-dihydroxy-N-(4-pyridylmethyl)-cyclopentanecarboxamide The title compound was prepared according to the method of example 39, step b) using the product of step a).

Mpt 130–135° C.

MS (APCI) 513 (M+H$^+$, 100%).

NMR δH (d$_6$-DMSO) 9.09–9.08 (1H, m), 8.56–8.48 (2H, m), 7.20–7.19 (2H, m), 5.35–4.43 (6H, m), 4.21–4.20 (1H, m), 3.38–3.32 (2H, m), 3.18–3.00 (4H, m), 2.47–2.28 (2H, m), 1.74–1.66 (2H, m), 1.15–0.94 (7H, m), 0.78–0.68 (3H, m).

EXAMPLE 90

[1S-[1α,2β,3β,4α(1S*,2R*)]]-N-Ethyl-2,3-dihydroxy-4-[5-(propylthio)-7-[3-(3-pyridylpropyl)amino]-3H-1,2,3-triazolo[4,5-d]pyrimidin-3-yl]-cyclopentanecarboxamide a) [3aR-[3aα,4α,6α(1R*,2S*),6aα]]-N-Ethyl-tetrahydro-2,2-dimethyl-6-[5-(propylthio)-7-[3-(3-pyridyl)propylamino]-3H-1,2,3-triazolo[4,5-d]pyrimidin-3-yl]-4H-cyclopenta-1,3dioxole-4carboxamide The subtitle compound was prepared according to the method of example 50, step a) using the product of example 7, step d) and 3-(3-pyridyl)propylamine (prepared as described by E. M. Hawes J. Heterocycl. Chem. 1973, 10, 39).

MS (APCI) 542 (M+H$^+$, 100%).

[1S-[1α,2β,3β,4α(1S*,2R*)]]-N-Ethyl-2,3-dihydroxy-4-[5-(propylthio)-7-[3-(3-pyridylpropyl)amino]-3H-1,2,3-triazolo[4,5-d]pyrimidin-3-yl]-cyclopentanecarboxamide The title compound was prepared according to the method of example 18, step b) using the product of step a).

Mpt 158° C.

MS (APCI) 501 (M+H$^+$, 100%).

NMR δH (d$_6$-DMSO) 9.05 (1H, t), 8.46 (1H, d) 8.40 (1H, dd), 7.92 (1H, t), 7.68–7.65 (1H, m), 7.31 (1H, dd), 5.11 (1H, d), 4.98–4.93 (2H, m), 4.45–4.40 (1H, m), 4.12–4.09 (1H, m), 3.52 (2H, q), 3.12–3.03 (4H, m), 2.74–2.66 (3H, m), 2.38–2.19 (2H, m), 1.98–1.92 (2H, m), 1.72–1.63 (2H, m), 1.03 (3H, t), 0.96 (3H, t).

EXAMPLE 91

[1S-[1α,2β,3β,4α(1S*,2R*)]]-N-Ethyl-2,3-dihydroxy-4-[5-(propylthio)-7-[4-[(3-pyridyl)butyl]amino]-3H-1,2,3-triazolo[4,5-d]pyrimidin-3-yl]-cyclopentanecarboxamide a) [(3aR-[3aα,4α,6α(1R*,2S*),6aα]]-N-Ethyl-tetrahydro-2,2-dimethyl-6-[5-(propylthio)-7-[4-[(3-pyridyl)butyl)amino]3H-1,2,3-triazolo[4,5-d]pyrimidin-3-yl]-4H-cyclopenta-1,3dioxole-4carboxamide Prepared according to the method of example 50, step a) using the product of example 7, step d) and 4-(3-pyridyl)butylamine (prepared as described by E M Hawes J. Heterocycl. Chem. 1973 10, 39).

MS (APCI) 555 (M+H$^+$, 100%).

b) [1S-[1α,2β,3β,4α(1S*,2R*)]]-N-Ethyl-2,3-dihydroxy-4-[5-(propylthio)-7-[4-[(3-pyridyl)butyl]amino]-3H-1,2,3-triazolo[4,5-d]pyrimidin-3-yl]-cyclopentanecarboxamide The title compound was prepared according to the method of example 18, step b) using the product of step a).

Mpt 175° C.

MS (APCI) 515 (M+H$^+$, 100%).

NMR δH (d$_6$-DMSO) 9.02 (1H, t), 8.43 (1H, d), 8.39 (1H, d), 7.92 (1H, t), 7.63 (1H, d), 7.29 (1H, dd), 5.11 (1H, d), 4.98–4.93 (2H, m), 4.45–4.40 (1H, m), 4.12–4.00 (1H, m), 3.56–3.50 (2H, d), 3.12–3.05 (4H, m), 2.80–2.63 (3H, m), 2.32–2.25 (2H, m), 1.72–1.64 (6H, m), 1.05–0.93 (6H, m).

EXAMPLE 92

[1S-[1α,2β,3β,4α(1S*,2R*)]]-N-Ethyl-2,3-dihydroxy-4-[7-[[2-(4-methylaminosulfonylphenyl)-cyclopropyl]amino]-5-(propylthio)-3H-1,2,3-triazolo[4,5-d]pyrimidin-3-yl]-cyclopentanecarboxamide a) (1S-trans)-N-Methyl-4-(2-Aminocyclopropyl)phenylsulfonamide, hydrochloride The sub-title compound was prepared from (1R-trans)-phenylcyclopropanamine according to the method described in U.S. Pat. No. 3,522,302 m.p. 190–2° C.

NMR δH (d$_6$-DMSO) 8.66 (3H, s), 7.68 (2H, d), 7.45 (1H, q), 7.38 (1H, s), 2.49–2.45 (1H, m), 2.38 (3H, d), 1.55–1.49 (1H, m), 1.34–1.28 (1H, m).

b) [1S-[1α,2β,3β,4α(1S*,2R*)]]-N-Ethyl-2,3-dihydroxy-4-[7-[[2-(4-methylaaminosulfonylphenyl)-cyclopropyl]amino]-5-(propylthio)-3H-1,2,3-triazolo[4,5-d]pyrimidin-3-yl]-cyclopentanecarboxamide The title compound was prepared according to the method of Example 7, step (e) using the products of step (a) and Example 7, step (d).

MS (APCI) 591 (M+H$^+$, 100%)

NMR δH (d$_6$-DMSO) 9.42 (1H, d), 7.93 (1H, t), 7.68 (2H, d), 7.44–7.34 (3H, m), 5.03 (1H, s), 4.96 (1H, q), 4.43 (1H, t), 4.10 (1H, t), 3.50–3.20 (2H, m), 3.10 (2H, quintet) 289.–2.69 (3H, m), 2.40 (3H, d), 1.71–1.63 (1H, m), 1.50–1.39 (3H, m), 1.03 (3H, t), 0.78 (3H, t).

Pharmacological Data

The preparation for the assay of the P$_{2T}$-receptor agonist/antagonist activity in washed human platelets for the compounds of the invention was carried out as follows.

Human venous blood (100 ml) was divided equally between 3 tubes, each containing 3.2% trisodium citrate (4 ml) as anticoagulant. The tubes were centrifuged for 15 minutes at 240 G to obtain a platelet-rich plasma (PRP) to which 300 ng/ml prostacyclin was added to stabilize the platelets during the washing procedure. Red cell free PRP was obtained by centrifugation for 10 minutes at 125 G followed by further centrifugation for 15 minutes at 640 G. The supernatant was discarded and the platelet pellet resuspended in modified, Calcium Free Tyrode solution (10 ml) (CFT), composition: NaCl 137 mM, NaHCO$_3$ 11.9 mM, NaH$_2$PO$_4$ 0.4 mM, KCl 2.7 mM, MgCl$_2$ 1.1 mM, dextrose 5.6 mM, gassed with 95% O$_2$/5% CO$_2$ and maintained at 37° C. Following addition of a further 300 ng/ml PGI$_2$, the pooled suspension was centrifuged once more for 15 minutes at 640 G. The supernatant was discarded and the platelets resuspended initially in 10 ml CFT with further CFT added to adjust the final platelet count to 2×10$^5$/ml. This final suspension was stored in a 60 ml syringe at 3° C. with air excluded. To allow recovery from PGI$_2$-inhibition of normal function, platelets were used in aggregation studies no sooner than 2 hours after final resuspension.

In all studies, 3 ml aliquots of platelet suspension were added to tubes containing CaCl$_2$ solution (60 μl of 50 mM solution with a final concentration of 1 mM). Human fibrinogen (Sigma, F 4883) and 8-sulphophenyltheophylline (8-SPT which was used to block any $P_1$-agonist activity of compounds) were added to give final concentrations of 0.2 mg/ml (60 µl of 10 mg/ml solution of clottable protein in saline) and 300 nM (10 µl of 15 mM solution in 6% glucose), respectively. Platelets or buffer as appropriate were added in a volume of 150 µl to the individual wells of a 96 well plate. All measurements were made in triplicate in platelets from each donor.

The agonist/antagonist potency was assessed as follows.

Aggregation responses in 96 well plates were measured using the change in absorbance given by the plate reader at 660 nm. Either a Bio-Tec Ceres 900C or a Dynatech MRX were used as the plate reader.

The absorbance of each well in the plate was read at 660 nm to establish a baseline figure. Saline or the appropriate solution of test compound was added to each well in a volume of 10 µl to give a final concentration of 0, 0.01, 0.1, 1, 10 or 100 mM. The plate was then shaken for 5 min on an orbital shaker on setting 10 and the absorbance read at 660 nm. Aggregation at this point was indicative of agonist activity of the test compound. Saline or ADP (30 mM; 10 µl of 450 mM) was then added to each well and the plate shaken for a further 5 min before reading the absorbance again at 660 nm.

Antagonist potency was estimated as a % inhibition of the control ADP response to obtain an $IC_{50}$. Compounds exemplified have $pIC_{50}$ values of more than 5.0

What is claimed is:

1. A compound of formula (I)

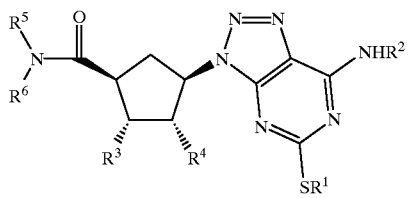

(I)

wherein:

$R^1$ is a $C_{1-6}$ alkyl, $C_{2-6}$ alkenyl, $C_{2-6}$ alkynyl, $C_{3-8}$-cycloalkyl, aryl or a thienyl group, each group being optionally substituted by one or more substituents selected from halogen, $OR^8$, $NR^9R^{10}$, $SR^{11}$ or $C_{1-6}$ alkyl (itself optionally substituted by one or more halogen atoms);

$R^2$ is $C_{1-8}$ alkyl, $C_{2-8}$ alkenyl or $C_{3-8}$ cycloalkyl each of which may be optionally substituted by one or more substituents selected from halogen, $OR^8$, $NR^9R^{10}$, $SR^{11}$, $C_{1-6}$ alkyl, $C_{3-8}$ cycloalkyl, pyridyl or aryl (the latter two of which may be optionally substituted by one or more substituents selected from halogen, $OR^{20}$, $C(O)R^{11}$, $NR^{14}C(O)R^{15}$, $NR^{16}SO_2R^{17}$, $SO_2NR^{18}R^{19}$, nitro, $NR^{12}R^{13}$, $SR^{11}$, methylenedioxy or $C_{1-6}$ alkyl which is optionally substituted by one or more halogen atoms);

$R^3$ and $R^4$ are both hydoxy;

$R^5$ is hydrogen or $C_{1-6}$ alkyl; $R^6$ is $C_{1-6}$ alkyl, optionally substituted by one or more groups selected from $C_{1-6}$ alkyl, $C_{2-6}$ alkenyl, $C_{2-6}$ alkynyl, halogen, $OR^{21}$, $C_{3-6}$ cycloalkyl, or $R^6$ is $C_{3-6}$ cycloalkyl, or $R^6$ is —A-phenyl or —A-pyridyl each of which may be optionally substituted by one or more groups selected from $C_{1-6}$ alkyl, $C_{2-6}$ alkenyl, $C_{2-6}$ alkynyl, halogen, $OC_{1-6}$ alkyl, $C_{3-6}$ cycloalkyl, or methylenedioxy; or $R^5$ and $R^6$ together with the nitrogen atom to which they are attached for a 5 to 7-membered saturated ring optionally substituted by $C_{1-6}$ alkyl;

A is a bond or $C_{1-6}$ alkyl;

$R^8$ is hydrogen, $C_{1-6}$ alkyl (which may be optionally substituted by one or more halogen atoms) or aryl (which may be optionally substituted by one or more substituents selected from halogen, nitro, $C(O)R^{11}$, $OR^{20}$, $SR^{11}$, $NR^{12}R^{13}$, $NR^{14}C(O)R^{15}$, $NR^{16}SO2R^{17}$, $SO2NR^{18}R^{19}$);

$R^9$ is hydrogen, $C_{1-4}$ alkyl (which may be optionally substituted by one or more halogen atoms) or aryl (which may be optionally substituted by one or more substituents selected from halogen, nitro, $C(O)R^{20}$, $OR^{20}$, $SR^{11}$, $NR^{12}R^{13}$, $NR^{14}C(O)R^{15}$, $NR^{16}SO_2R^{17}$, $SO_2NR^{18}R^{19}$);

$R^{10}$ is hydrogen, $C_{1-6}$ alkyl or $C(O)C_{1-6}$ alkyl;

$R_{12}$ and $R_{13}$ are independently hydrogen, $C_{1-6}$ alkyl or together with the nitrogen atom to which they are attached form a 4- to 8-membered ring;

$R^{15}$ is $C_{1-6}$ alkyl or phenyl;

$R^{11}$, $R^{14}$ and $R^{16}$ are independently hydrogen or $C_{1-6}$ alkyl;

$R^{17}$ is $C_{1-6}$ alkyl or phenyl;

$R^{18}$ and $R^{19}$ are independently hydrogen, $C_{1-6}$ alkyl or phenyl;

$R^{20}$ is hydrogen, phenyl or $C_{1-6}$ alkyl (which may be optionally substituted by halogen);

$R^{21}$ is hydrogen or $C_{1-6}$ alkyl, provided that when $R^{21}$ is H, $R^5$ must be $C_{1-6}$ alkyl;

or a pharmaceutically acceptable salt or solvate thereof.

2. A compound according to claim 1 in which $R^1$ is $C_{1-6}$ alkyl, thienyl or trifluoromethylphenyl.

3. A compound according to claim 1 in which $R^2$ is $C_{1-6}$ alkyl or a $C_{3-8}$-cycloalkyl group optionally substituted by phenyl which itself can be optionally substituted by halogen, $OR^8$ or $C_{1-6}$-alkyl.

4. A compound according to claim 1 in which $R^5$ is hydrogen and $R^6$ is cyclopropyl, methylcyclopropyl or $C_{1-6}$ alkyl substituted by one or more fluoro atoms or $R^5$ and $R^6$ together with the nitrogen atom to which they are attached form a pyrrolidine ring.

5. A compound according to claim 1 in free base form and as a pharmaceutically acceptable salt or solvate thereof.

6. A pharmaceutical composition comprising a compound according to claim 1 in combination with a pharmaceutically acceptable diluent, adjuvent or carrier.

7. A process for the preparation of a compound of formula (I) which comprises:

(a) reaction of a compound of formula (II):

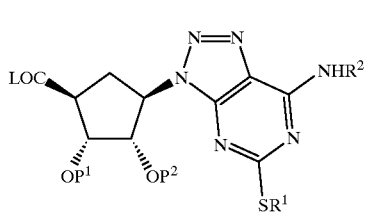

(II)

where $R^1$ and $R^2$ are as defined in formula (I), or are protected derivatives thereof, $P^1$ and $P^2$ are hydrogen or protecting groups and L is a leaving group, with a compound of formula (III):

$R^5R^6NH$ (III)

where $R^1$ and $R^2$ are defined inn formula (I), or
(b) reacting a compound of formula (IV):

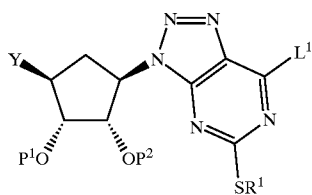

wherein Y is $CO_2H$, $CO_2R'$ or $CONR^5R^6$ and $R^1$, $R^5$, $R^6$, $P^1$ and $P^2$ are as defined above and $L^1$ is a leaving group and R' is a $C_{1-6}$-alkyl or benzyl group, with an amine $NH_2R^2$ or a salt of $NH_2R^2$ wherein $R^2$ is as defined above and optionally thereafter (a) or (b) and in any order:
    converting one or more functional groups into a further functional groups
    removing any protecting groups
    forming a pharmaceutically acceptable salt or solvate.

8. A method of treating myocardial infarction in a patient in need of such treatment, said method comprising the step of administering to said patient an effective amount of a compound as claimed in claim 1.

9. A method of treating unstable angina in a patient in need of such treatment, said method comprising the step of administering to said patient an effective amount of a compound according to claim 1.

* * * * *